US008617120B2

(12) United States Patent
Rowe et al.

(10) Patent No.: US 8,617,120 B2
(45) Date of Patent: Dec. 31, 2013

(54) INTEGRATED SYRINGE DEVICE WITH SELF-CAPPING CONNECTOR

(75) Inventors: David T. Rowe, Sinking Spring, PA (US); Rodney W. Denlinger, Lancaster, PA (US); Joel S. Rosenblatt, Pottstown, PA (US); Nisha Gupta, Audubon, PA (US); Joseph A. Runkle, Lititz, PA (US); Jeffrey M. Vitullo, Pottstown, PA (US); Philip D. Schmidt, Rougemont, NC (US); William J. Vojtasek, Wyomissing, PA (US)

(73) Assignee: Arrow International, Inc., Reading, PA (US)

( * ) Notice: Subject to any disclaimer, the term of this patent is extended or adjusted under 35 U.S.C. 154(b) by 0 days.

(21) Appl. No.: 13/398,480

(22) Filed: Feb. 16, 2012

(65) Prior Publication Data
US 2012/0271278 A1    Oct. 25, 2012

Related U.S. Application Data

(60) Provisional application No. 61/443,990, filed on Feb. 17, 2011.

(51) Int. Cl.
*A61M 5/32* (2006.01)
*A61M 5/178* (2006.01)
*A61M 5/00* (2006.01)

(52) U.S. Cl.
USPC .................. 604/192; 604/263; 604/164.08

(58) Field of Classification Search
USPC ............ 604/263, 164.08, 533, 513, 220, 192, 604/197–198; 215/272–291; 401/98, 159, 401/61
See application file for complete search history.

(56) References Cited

U.S. PATENT DOCUMENTS

| | | | | |
|---|---|---|---|---|
| 3,945,734 | A * | 3/1976 | Woodbridge | 401/198 |
| 4,921,490 | A * | 5/1990 | Spier et al. | 604/192 |
| 2007/0078429 | A1* | 4/2007 | Sharp | 604/411 |
| 2010/0137810 | A1* | 6/2010 | Chandrasekaran et al. | 604/198 |
| 2011/0152841 | A1* | 6/2011 | Nemoto | 604/533 |
| 2012/0130351 | A1* | 5/2012 | Alvain | 604/533 |
| 2013/0144219 | A1* | 6/2013 | Evans et al. | 604/192 |

* cited by examiner

*Primary Examiner* — Nicholas Lucchesi
*Assistant Examiner* — Rebecca E Eisenberg
(74) *Attorney, Agent, or Firm* — Baker & Hostetler LLP

(57) ABSTRACT

An embodiment in accordance with the present invention provides an integrated syringe-device which can store a volume of fluid for infusion, can connect via an air-tight connector to another device (such as a luer connector), can flush fluid through the connector into the other device, and can deliver a cap that forms an air-tight closure to the device connector.

13 Claims, 29 Drawing Sheets

INTEGRATED SYRINGE DEVICE WITH SELF-CAPPING CONNECTOR

CROSS-REFERENCE TO RELATED APPLICATIONS

This application claims priority to and is a non-provisional of U.S. provisional patent application entitled, INTEGRATED SYRINGE DEVICE WITH SELF-CAPPING CONNECTOR, filed Feb. 17, 2011, having a Ser. No. 61/443,990, the disclosure of which is hereby incorporated by reference in its entirety.

FIELD OF THE INVENTION

The present invention relates generally to a medical apparatus. More particularly, the present invention relates to a syringe device for use with an indwelling medical device.

BACKGROUND OF THE INVENTION

Indwelling medical devices such as an indwelling catheter are inserted within the body for prolonged periods of time. As an indwelling catheter can remain in the body without being in active use, the port of entry for infusions can be closed. Many devices, including vascular catheters, frequently use luer connectors to be able to connect infusion devices such as syringes. When an indwelling catheter is not in use, a cap that provides an airtight seal can be utilized to prevent access by unwanted fluids, gases, or microbes.

Additionally, indwelling medical devices such as indwelling catheters and vascular catheters are prone to causing catheter-related infections. For instance, contamination of the catheter hub and subsequent colonization of catheters by microbes as well as formation of a bacterial biofilm on the external and internal surfaces are common causes for catheter related infections. Catheter related blood stream infections (CRBSI) are caused by intraluminal contaminants. Therefore, when a vascular catheter is not in use it can be filled with fluid and the connector at the end of the vascular catheter can be capped, in a procedure known as catheter locking. Catheter locking also provides a hydraulic barrier to formation of air pockets, which if subsequently flushed can cause emboli. Catheter lock solutions containing salts of citrate, ethanol, EDTA, antibiotics, and methylene blue are commonly used. Most of these lock solutions decrease the occurrences of CRBSI, when the solutions indwell for extended periods of time while the lumen is not in use. However, locking and flushing catheters can require a health care provider to execute numerous steps. These steps can include removing a cap from the luer of an extension line, affixing an infusing device (typically a syringe) containing the fluid to be infused, infusing the fluid into the lumen of the catheter using positive pressure, removing the infusion device, and recapping the luer. During the course of performing these steps it is possible for a health care provider to drop or misplace components, or for the components to become contaminated with microbes. This is especially possible with smaller components such as the luer cap itself.

It would therefore be advantageous to provide a device and method that solves the aforementioned problems and would eliminate the steps of detaching the delivery device and then obtaining a separate cap to provide closure until further use is necessary.

SUMMARY OF THE INVENTION

The foregoing needs are met, to a great extent, by the present invention, wherein in one aspect a fluid delivery device and recapping device are provided in one apparatus.

In accordance with one aspect of the present invention, an apparatus for infusing liquid and sealing an indwelling medical device includes a syringe body having an outer wall defining a lumen extending therethrough for holding an infusing liquid and further including a proximal end and a distal end and wherein the outer wall defines an opening at the distal end of the syringe body. The apparatus can also include a plunger slidably disposed within the lumen of the syringe, such that the plunger slides from the proximal end of the syringe body to the distal end of the syringe body. The apparatus further includes a first notch defined by the outer wall of the syringe body and positioned proximate of the opening at the distal end of the syringe body and a pinch release ring having a finger which couples with the first notch and a wing to provide leverage to remove the finger from the first notch. A cap defining an opening through which the infusing liquid can travel can be disposed within the opening at the distal end of the syringe body configured to couple to an end of the indwelling medical device. The cap can define a second notch with which the finger of the pinch release ring can couple. A plunger seal can also be disposed at a proximal end of the plunger, and configured to be separable from the proximal end of the plunger and coupleable to the cap, such that the cap is sealed when coupled to the plunger seal.

In accordance with another embodiment of the present invention, an apparatus for infusing liquid and sealing an indwelling medical device includes a syringe body having an outer wall defining a lumen extending therethrough and further including a proximal end and a distal end and wherein the outer wall defines an opening at the distal end of the syringe body. A plunger can be slidably disposed within the lumen of the syringe body, such that the plunger slides from the proximal end of the syringe to the distal end of the syringe body. A cap can be disposed at the distal end of the syringe body within the opening of the lumen defined by the outer wall of the syringe body and can be configured to couple to an end of the indwelling medical device. The cap can also be configured to be separated from the syringe body. A plunger seal can be disposed at a proximal end of the plunger and can be configured to be separable from the proximal end of the plunger and coupleable to the cap, such that the cap is sealed. The device can also include a twist clamp for securing the cap to the distal end of the syringe body.

In accordance with yet another embodiment of the present invention, an apparatus for infusing liquid and sealing an indwelling medical device includes a syringe body having an outer wall defining a lumen extending therethrough and further including a proximal end and a distal end and wherein the outer wall defines an opening at the distal end of the syringe body. A cap can be disposed at the distal end of the syringe body within the opening and the lumen defined by the outer wall of the syringe body. The cap can also be configured to couple to an end of the indwelling medical device and to be separated from the syringe body. A plunger having an elongate shaft with a proximal end and a distal end can be slidably disposed within the lumen of the syringe body, such that the plunger slides from the proximal end of the syringe to the distal end of the syringe body. Additionally, the apparatus can include a sealing pin disposed at the proximal end of the plunger configured to be coupled to the cap to form a seal, wherein the sealing pin is removable from the proximal end of the plunger.

In accordance with still another embodiment of the present invention an apparatus for infusing liquid and sealing an indwelling medical device includes a syringe body having an outer wall defining a lumen extending therethrough and further including a proximal end and a distal end and wherein the outer wall defines an opening at the distal end of the syringe body. The device can include a cap disposed at the distal end of the syringe body within the opening and the lumen defined by the outer wall of the syringe body configured to couple to an end of the indwelling medical device and wherein the cap is configured to be separated from the syringe body. A plunger having an elongate shaft with a proximal end and a distal end slidably can be disposed within the lumen of the syringe body, such that the plunger slides from the proximal end of the syringe to the distal end of the syringe body. A sealing ball can be disposed at the proximal end of the plunger configured to be coupled to the cap to form a seal, wherein the sealing ball is removable from the proximal end of the plunger.

In accordance with yet another embodiment of the present invention, an apparatus for infusing liquid and sealing an indwelling medical device includes a syringe body having an outer wall defining a lumen extending therethrough and further including a proximal end and a distal end and wherein the outer wall defines an opening at the distal end of the syringe body and defines fingers disposed at the distal end of the syringe body. A cap can be disposed at the distal end of the syringe body within the opening of the lumen defined by the outer wall of the syringe body. The cap can be configured to couple to an end of the indwelling medical device, and the cap can also be configured to include a cap seal. A plunger having an outer wall defining a hollow elongate shaft with a proximal end and a distal end can be slidably disposed within the lumen of the syringe body, such that the plunger slides from the proximal end of the syringe to the distal end of the syringe body. The device can also include a sliding lock disposed at the distal end of the syringe body. The sliding lock can be slidably disposed to frictionally hold the fingers around the cap in a first position and to release the fingers from around the cap in a second position.

In accordance with still another embodiment of the present invention, a method for locking an indwelling medical device includes pulling a plunger back from a distal most position within a barrel of a syringe to a proximal position within the barrel of the syringe to transfer lock solution from a reservoir within the plunger to the barrel of the syringe. The method can also include depressing the plunger to a first predetermined point within the barrel of the syringe to purge air from the syringe barrel. Further the method includes coupling the syringe to the indwelling medical device via an end cap disposed at a distal end of the syringe. Also, the method includes depressing the plunger to a second predetermined point within the barrel of the syringe to flush the lock solution into the indwelling medical device, and disengaging the syringe from the end cap such that the end cap remains coupled to the catheter.

DETAILED DESCRIPTION

Figure 1:
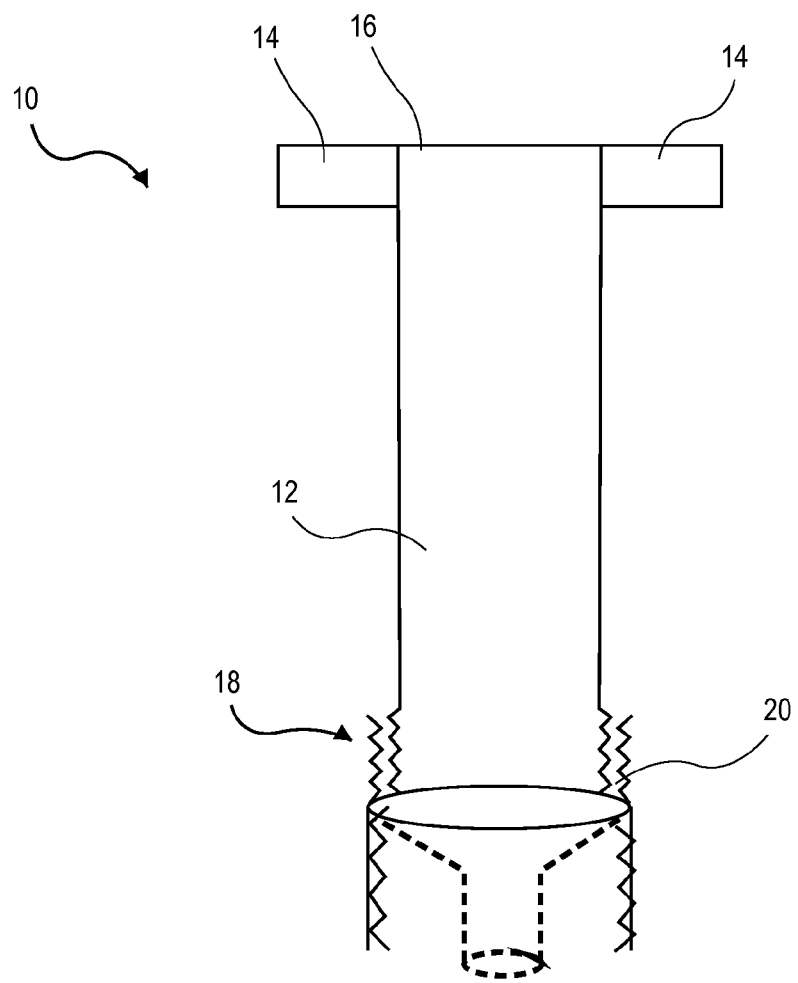
FIG. 1 illustrates a portion of an integrated syringe device with self-capping connector in accordance with an embodiment of the invention.

The invention will now be described with reference to the drawing figures, in which like reference numerals refer to like parts throughout. An embodiment in accordance with the present invention provides an integrated syringe-device which can store a volume of fluid for infusion, can connect via an air-tight connector to another device (such as a luer connector), can flush fluid through the connector into the other device, and can deliver a cap that forms an air-tight closure to the device connector.

The integrated syringe device contains at least one chamber which can be prefilled with a liquid for infusion into the indwelling medical device. The integrated syringe device can contain a mated connector, which has a corresponding structure to a connector positioned on the indwelling medical device. Additionally, the integrated syringe device can include a drive mechanism capable of applying static pressure to infuse solution. A cap that can be readily separated from the delivery device can be coupled to the drive mechanism, while remaining on the indwelling medical device. The cap can engage the indwelling medical device after the drive mechanism has been engaged and the solution is infused. The cap can then be separated from the drive mechanism. The cap can be separated by unscrewing, sliding, or breaking it off from the drive mechanism. A break away cap can be made by pre-indenting or perforating along lines where fracture is desired. Engagement of the cap to the recipient luer connector can be achieved by a latching mechanism using a deformable or slightly elastic material that can subsequently create compression between the top and bottom of the cannula through the luer fitting.

An embodiment of the present inventive apparatus is illustrated in FIG. 1. FIG. 1 illustrates a barrel-like syringe infusion device 10. The syringe infusion device 10 includes a hollow barrel 12, flanges 14 for gripping at a proximal end 16 of the syringe 10 and a male luer-like connector 18 at a distal end 20 of the syringe 10. The male luer connector 18 can be separated from the barrel near the end either by unscrewing it, by sliding it off or by breaking it away. The barrel 12 can be filled with a fluid for infusion into the indwelling medical device.

Figure 2:
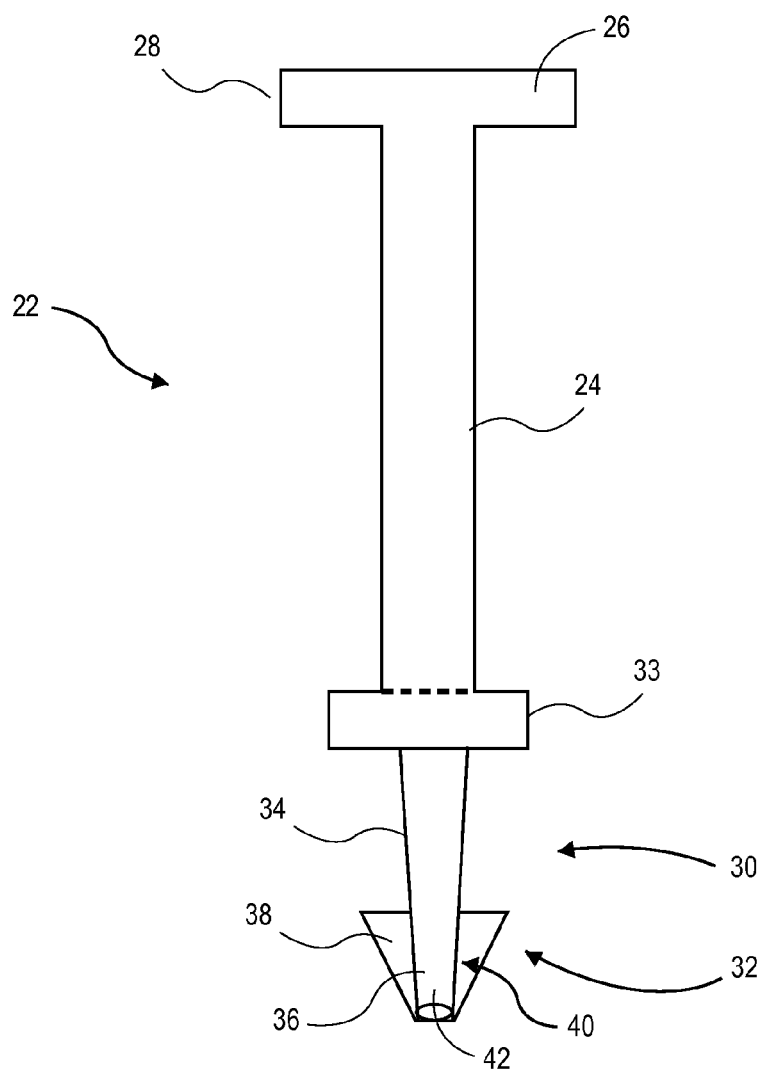
FIG. 2 illustrates another portion of an integrated syringe device with self-capping connector in accordance with an embodiment of the invention illustrated in FIG. 1.

A plunger drive 22 for the syringe infusion device 10 is depicted in FIG. 2. It consists of a shaft 24 with a thumb rest 26 for application of pressure at a proximal end 28 of the drive 22 and a plunger sealing element 30 at a distal end 32 extending from a plunger seal element 33 at the distal end of the shaft 24. Integrated into the plunger sealing element 30 is a smaller shaft 34 extending from the plunger seal element 33 to a tip 36 has a latch 38. The latch can be a mechanism located a distal end portion 32, or may be a particular configuration of the tip 36. Preferably, the latch 38 can be formed from an elastomeric material or any other material flexible enough to be driven through the tapered end of the luer connector on the barrel 12. Once latched, an airtight seal must be formed by the latch 38 against the distal tip of the barrel 12. This can be accomplished by compression of flange 40 of the latch 38 against base 42 of the plunger 22 and the inner surface of the distal tip of the barrel 12. The shaft 34 connecting the latch 40 to the base of the plunger 22 can be formed such that it is capable of sustaining a compressive seal. Preferably, the sealing element 30 can be separated from the shaft 24 once the latch 38 is engaged. Separation of the sealing element 30 from the shaft 24 can be by unscrewing a threaded connection, sliding off when retracted, by breaking at a pre-indented location, or any other means which allows the sealing element 30 to be separated from the shaft 24.

Figure 3:
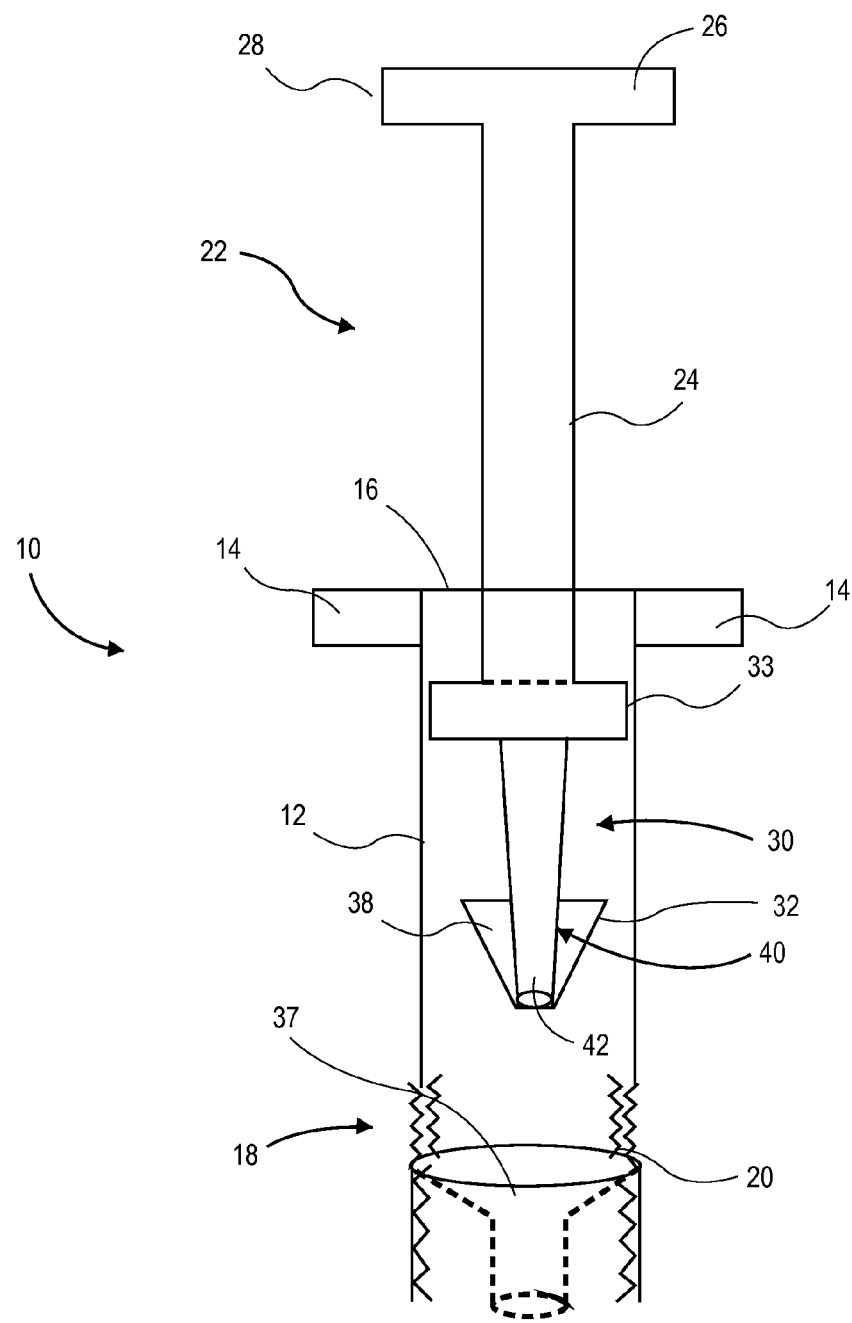
FIG. 3 illustrates an integrated syringe device with self-capping connector in accordance with an embodiment of the invention illustrated in FIGS. 1 and 2.
Figure 4:
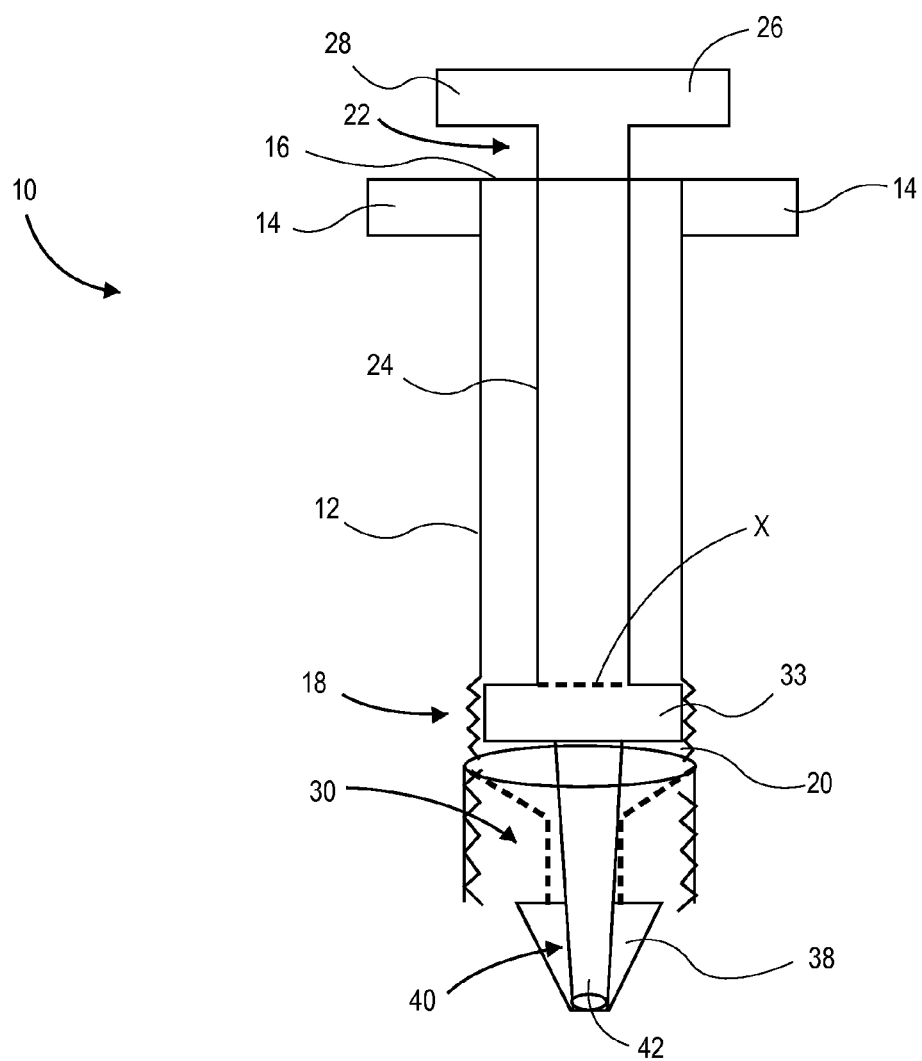
FIG. 4 illustrates another view of an integrated syringe device with self-capping connector in accordance with an embodiment of the invention illustrated in FIG. 3.

FIG. 3 illustrates the plunger 22 inside of the barrel 12 in a nondeployed position and FIG. 4 illustrates the syringe 10 with the plunger 22 fully depressed through the barrel 12, such that all of the infusion fluid has been injected into the indwelling medical device. In FIG. 3, the barrel 12 below the plunger seal 33 of the plunger 22 would typically be filled with the fluid for infusion. The plunger 22 fits within the barrel 12 of the syringe device 10 and is prefilled with a fluid for infusing into a catheter extension line and lumen. In the case of a catheter lock, the fluid volume is selected to match the internal volume of the extension line and lumen being filled. Following connection of the connector 18 on the barrel 12 to a female connector on an extension line the fluid is infused by a stroke of the plunger 22 relative to the barrel 12 as shown in FIG. 3. The latch 38 on the sealing element 30 is driven through the distal orifice 37 in the barrel 12, after which the fluid exits the barrel and the plunger 22 is fully deployed, as shown in FIG. 4. The proximal portion of barrel 12 and the plunger 22 can then be separated, leaving the distal portion closed over the medical device opening. The separation can occur at a separation line "X" shown in FIG. 4, at the distal end of the shaft 24. The sealing element 30, together with plunger seal 33 remains, as a cap assembly, which can be removed from the indwelling medical device via the luer-like connection 18.

Figure 5:
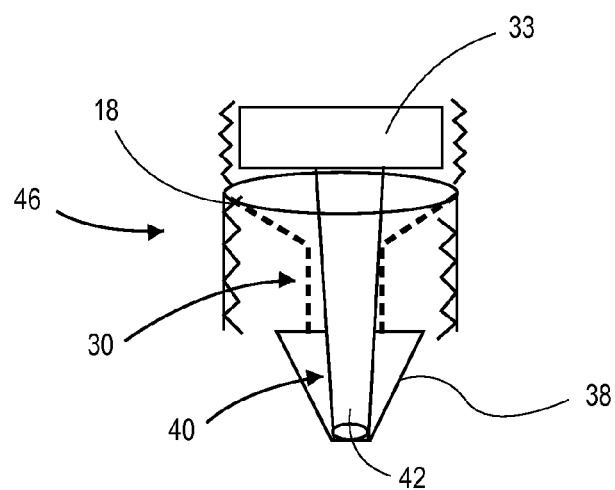
FIG. 5 illustrates another view of an integrated syringe device with self-capping connector in accordance with an embodiment of the invention illustrated in FIG. 1.
Figure 6B:
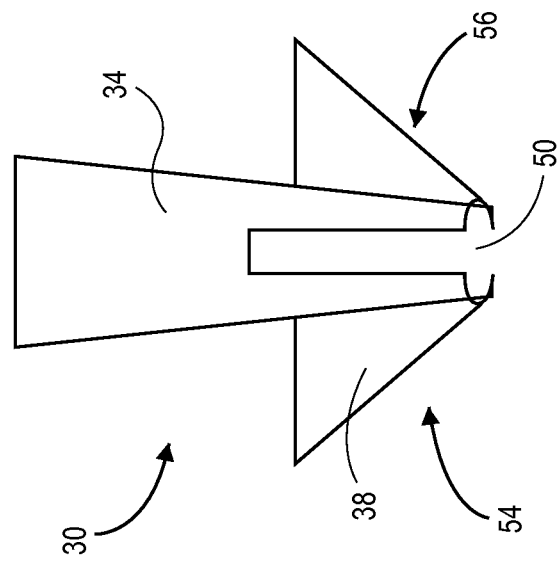
FIGS. 6*a* and 6*b* illustrate further features of an integrated syringe device with self-capping connector in accordance with an embodiment of the invention illustrated in FIGS. 1-5.
Figure 6A:
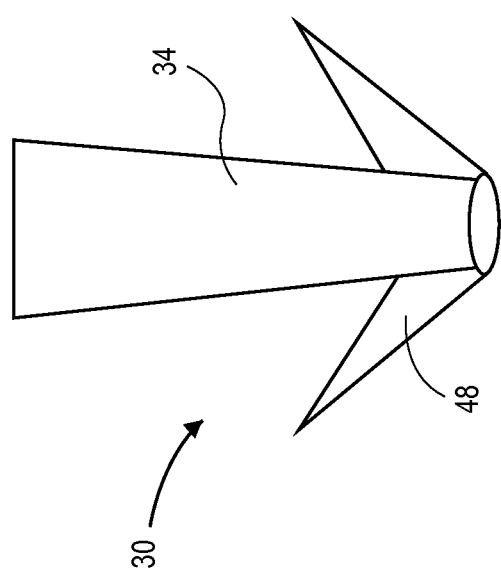

FIG. 5 illustrates a cap assembly 46 left behind on the indwelling medical device following separation of the separable parts of the barrel 12 and plunger 22. Various mechanisms can be provided for creating the compression of the latching element 38 illustrated in FIG. 2. One such example is to use an elastomeric flange. Another such example is to provide an arrow shaped flange 48 as illustrated in FIG. 6a. The arrows shaped flange 48 can deflect and snap back to its original positions once the sealing element 30 has gone through orifice 37. Yet another such example, is to provide a slit 50 in a shaft 34 of the sealing element 30, as illustrated in FIG. 6b. The slit 50 in the shaft 34 enables a left side 54 and a right side 56 of the sealing element 30 to deflect inward while being driven through orifice 37.

Figure 7A:
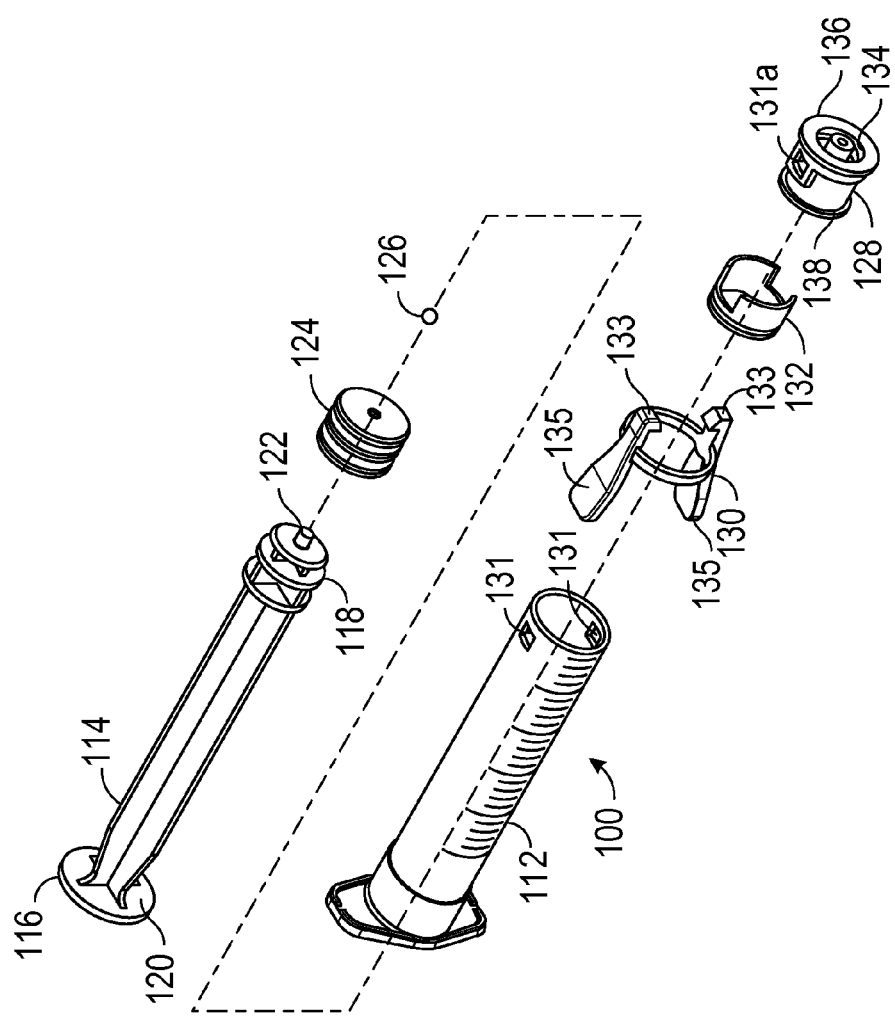
FIGS. 7*a*-7*e* illustrate an integrated syringe device with self-capping connector in accordance with another embodiment of the invention.

As illustrated in another embodiment of the invention, shown in FIG. 7a, a syringe device 100 can take the form of a prefilled syringe body 112 that utilizes a transferable ball for the purpose of infusing a lock solution and sealing the removable catheter cap in one step. The syringe body 112 includes a plunger shaft 114 which having a proximal end 116 and a distal end 118. The proximal end 116 of the plunger shaft 114 includes a thumb rest 120. The distal end 118 includes a plunger transfer pin 122 and a plunger seal 124. The plunger seal 124 also includes a ball 126 which can be transferred to a cap 128 when the plunger shaft 114 is pushed through the syringe 112. The cap 128 can be secured to the syringe body 112 via a pinch release ring 130, and the cap 128 can also be sealed to the syringe body 112 via the cap seal 132. The syringe body 112 includes notches 131, and cap seal 128 has corresponding notches, 131a, both of which can mate with fingers 133 of the pinch ring 130. Flanges 135 can be actuated to engage or disengage the fingers from the notches 131 or 131a. This seal can also be created by molding the cap 128 out of a soft durometer polymer with built in ribs that act as the cap seal. The syringe body 112 also includes flanges 106.

Figure 7B:
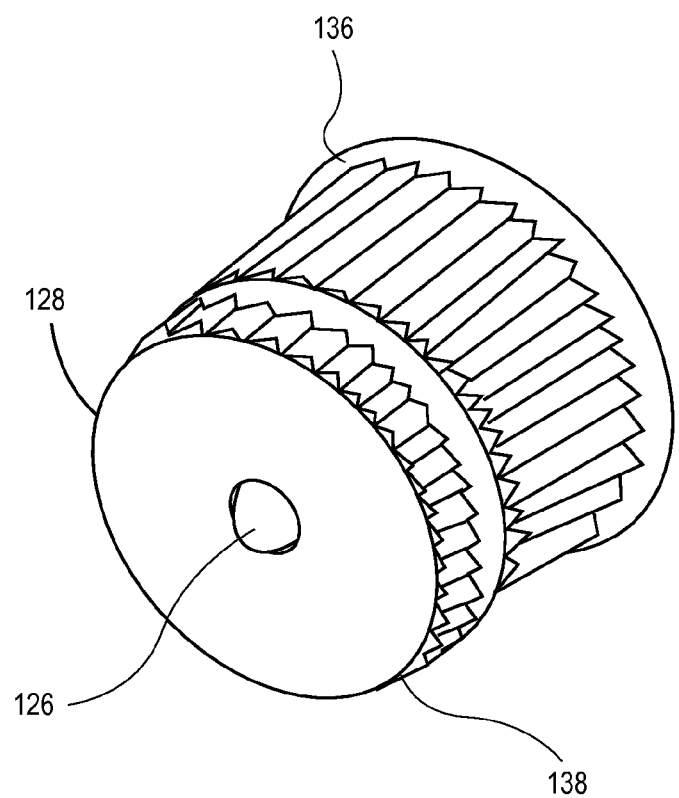

FIG. 7b illustrates the ball 126 pressed into the cap 128 creating the seal for the proximal or top side 138 of the cap 128. The plunger shaft 114, plunger transfer pin 122, plunger seal 124, syringe body 112 and the pinch release ring 130 are then disengaged from the cap 128 by pinching tabs 135 of the pinch release ring 130 and pulling the assembly from the cap 128, which remains as a seal to the luer of the indwelling medical device.

Figure 7C:
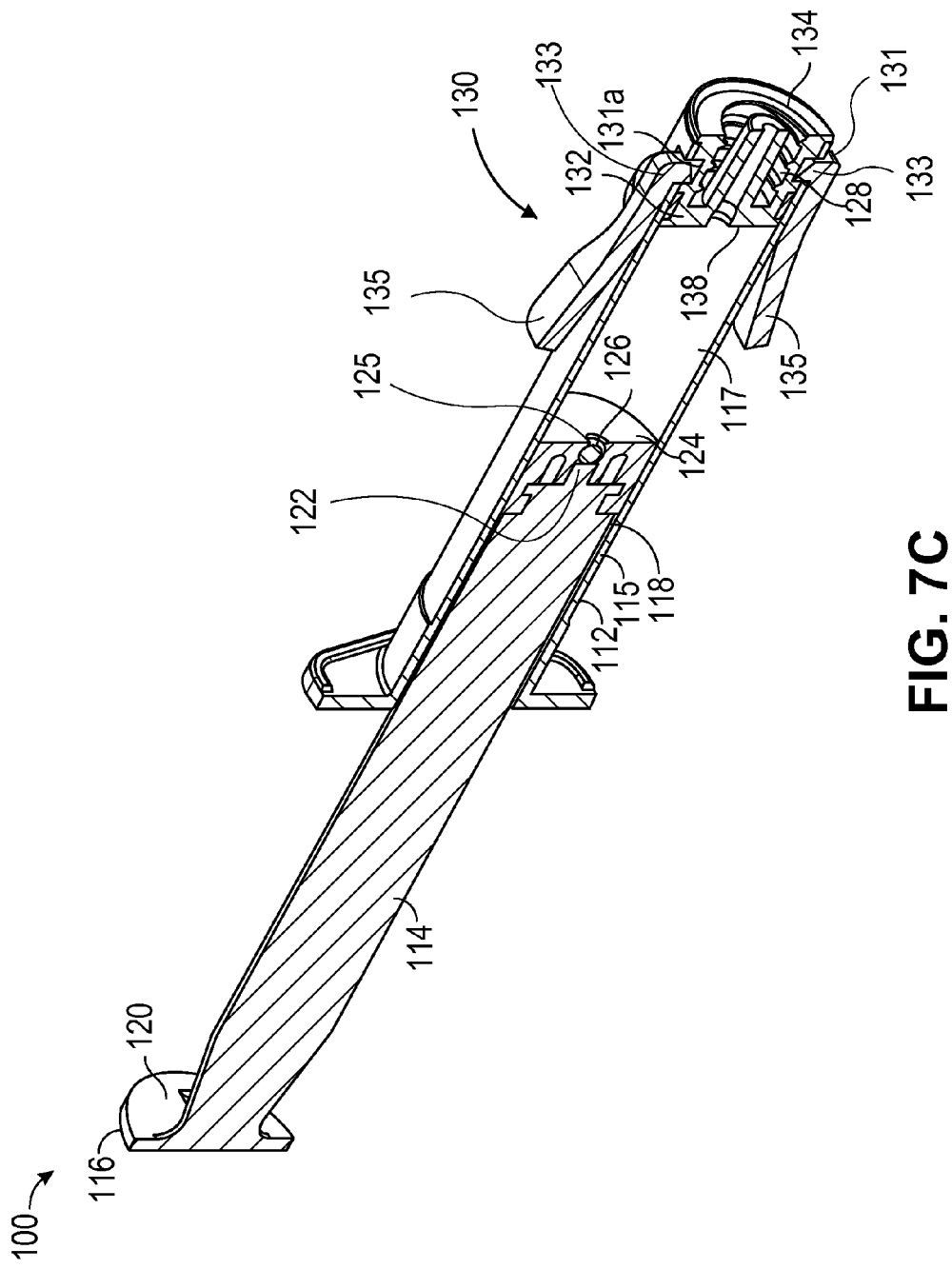

FIG. 7c illustrates a cross sectional view of the embodiment illustrated in FIGS. 7a and 7b. FIG. 7c shows the plunger shaft 114 disposed within a chamber 117 defined by the outer wall 115 of the syringe body 112. The plunger shaft 114 and the outer wall 115 of the syringe body 112 also define a chamber 117 for holding the lock solution. At the distal end 118 of the plunger 114 is the plunger transfer pin 122 and the plunger seal 124. The plunger seal 124 also includes the ball 126, which is seated within an opening 125 defined by the plunger seal 124. The ball 126 can be transferred to the cap 128 from its opening 125 in the plunger seal 124, when the plunger shaft 114 is pushed through the syringe body 112. The cap 128 can be secured to the syringe body 112 via the pinch release ring 130, and the cap 128 can also be sealed to the syringe body 112 via the cap seal 132. The syringe body 112 includes notches 131, and cap seal 128 has corresponding notches, 131a, both of which can mate with fingers 133 of the pinch ring 130. Flanges 135 can be actuated to engage or disengage the fingers from the notches 131 or 131a. This seal can also be created by molding the cap 128 out of a soft durometer polymer with built in ribs that act as the cap seal.

Figure 7D:
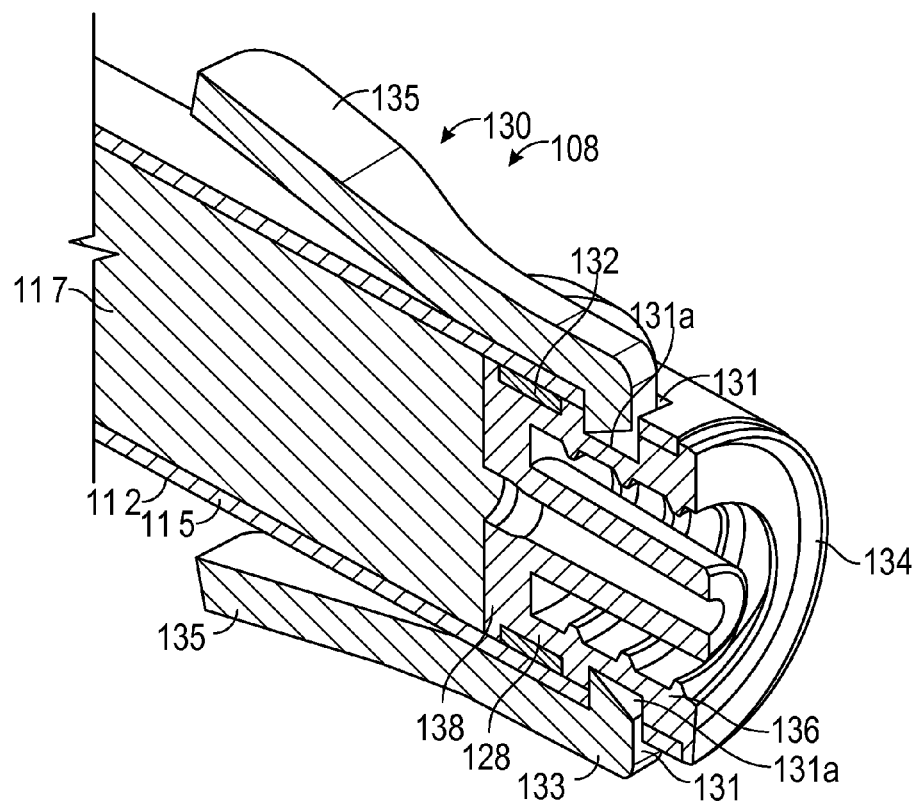

FIG. 7d illustrates a cross sectional view of a distal end 108 of the syringe body 112 in accordance with the embodiment illustrated in FIGS. 7a-7c. FIG. 7d shows the cap 128 disposed at the distal end 108 of the syringe body 112. The cap 128 can be held in place by the pinch release ring 130. The cap 128 can also be sealed to the syringe body 112 via the cap seal 132. The syringe body 112 includes notches 131, and cap seal 128 has corresponding notches, 131a, both of which can mate with fingers 133 of the pinch ring 130. Flanges 135 can be actuated to engage or disengage the fingers from the notches 131 or 131a. This seal can also be created by molding the cap 128 out of a soft durometer polymer with built in ribs that act as the cap seal.

FIGS. 7c-7d illustrate that the syringe device 100 can be secured to the desired luer hub of an indwelling medical device via a mating male luer connector 134 on a bottom side 136 of the cap 128. The lock solution can be injected into the indwelling medical device by depressing the plunger shaft 114 until the plunger seal 124 contacts the top side 138 of the cap 128. At this point, all lock solution has been transferred from the syringe body 112 through the cap 128 and into the indwelling medical device. Once contact is made a slight increase in force to the plunger shaft 114 can transfer the ball 126 from the plunger seal 124 into the cap 128 via a plunger transfer pin 122. This will provide a seal for the cap 128.

Figure 7E:
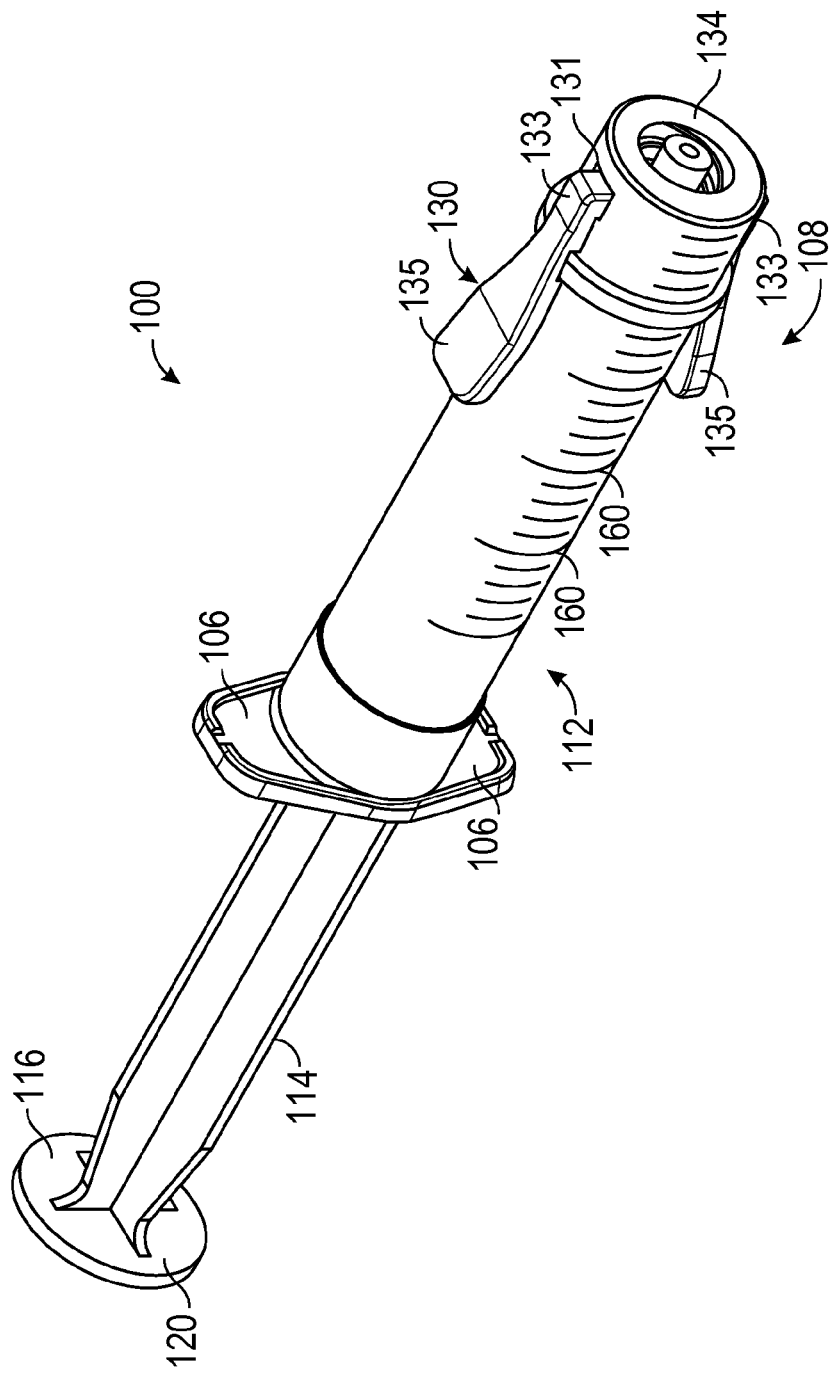

FIG. 7e illustrates the syringe device 100 in accordance with the embodiment of the invention illustrated in FIGS. 7a-7d. FIG. 7e shows the syringe body 112 and the plunger 114 partially disposed within the syringe body 112. The syringe body 112 includes markings 160 to indicate the amount of lock solution contained within the syringe body 112. The cap 128 (hidden in FIG. 7e) is disposed at the distal end 108 of the syringe body 112 and is held in place by the pinch ring 130. The syringe body 112 includes notches 131, which can mate with fingers 133 of the pinch ring 130. Flanges 135 can be actuated to engage or disengage the fingers from the notches 131 or 131a (hidden in FIG. 7e). Thumb rest 120 is disposed at the proximal end 116 of the plunger shaft 114 and can be used to move the plunger shaft 114 through the syringe body 112 to dispense the lock solution into the indwelling catheter. The syringe body 112 also includes flanges 106 to aid in dispensing the lock solution disposed in chamber 117 shown in FIG. 7c.

Figure 8A:
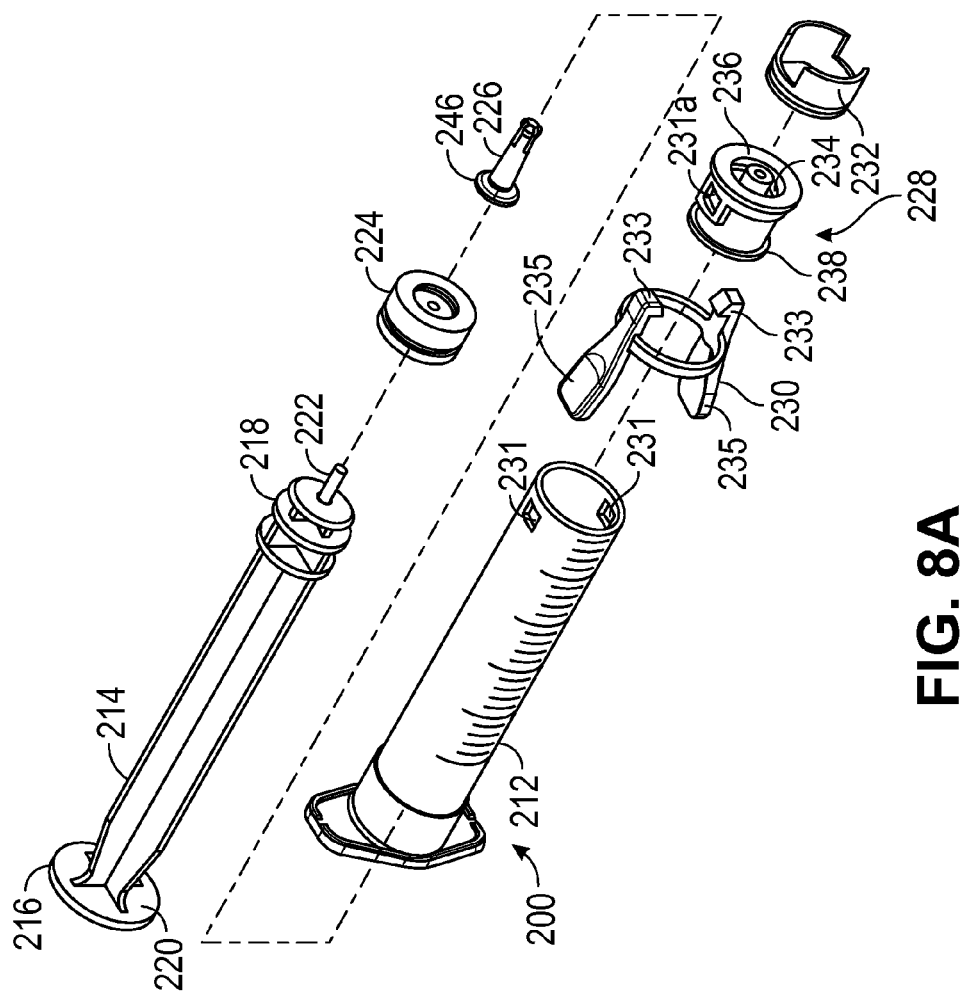
FIGS. 8*a*-8*e* illustrate an integrated syringe device with self-capping connector in accordance with yet another embodiment of the invention.

FIG. 8a is another embodiment of the invention and illustrates a pinch clamp 230 to detach a cap 228 from the syringe device 200. FIG. 8a also illustrates a tapered cap-sealing pin 226. The syringe device 200 includes a prefilled syringe body 212 that utilizes a sealing pin 226 for the purpose of infusing a lock solution and sealing the removable catheter cap 228 in one step. The device includes the syringe body 212 and includes a plunger shaft 214 having a proximal end 216 and a distal end 218. The proximal end 216 of the plunger shaft 214 includes a thumb rest 220. The distal end 218 includes or may be connected to a plunger transfer pin 222 and a plunger seal 224. The plunger seal 224 also includes a sealing pin 226 which can be transferred to a cap 228 when the plunger shaft 214 is pushed through the syringe 212. The cap 228 can be secured to the syringe body 212 via the pinch release ring 230, and the cap 228 can also be sealed to the syringe body 212 via the cap seal 232. In order to create the seal, the cap seal 232 can be formed in whole or in part from a soft durometer polymer. Alternatively, this seal can also be created by molding the cap 228 out of a soft durometer polymer with built in ribs that act as the cap seal. The cap 228 can be secured to the syringe body 212 via the pinch release ring 230 and the cap 228 is sealed to the syringe body 228 via ribs 244 (shown in FIG. 8c) molded directly on the cap 228. The syringe body 212 includes notches 231 and cap seal 228 has corresponding notches 231a, both of which can mate with fingers 233 of the pinch ring 230. Flanges 235 can be actuated to engage or disengage the fingers from the notches 231 or 231a.

Figure 8B:
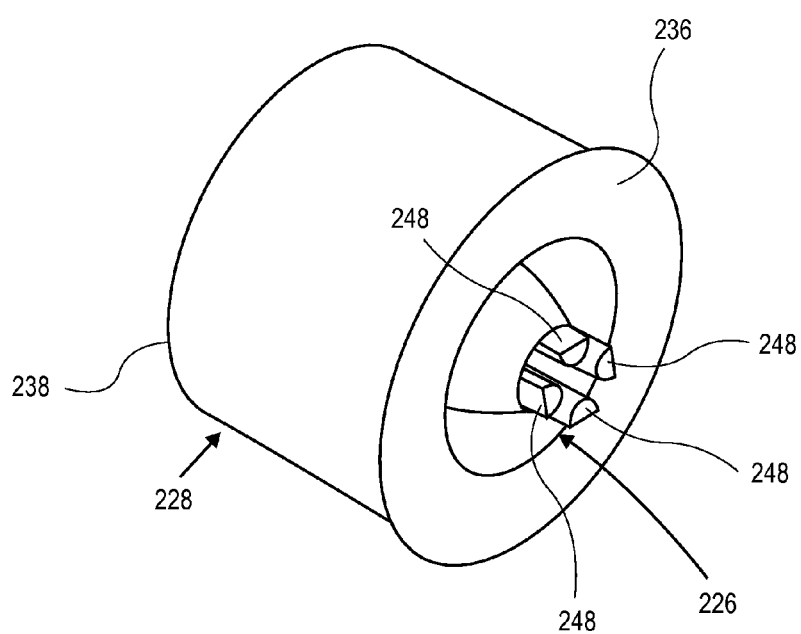

The device can be secured to the desired indwelling medical device luer hub via the mating male luer connector 234 on the bottom side 236 of the cap 228. As illustrated in FIG. 8b, the lock solution can be injected into the catheter by depressing the plunger shaft 214 until the sealing pin 226 is driven through the cap 228 and tabs 248 on the bottom side of the sealing pin 226 snap outward upon exiting the bottom side 236 of the cap 228. Once the tabs 248 on the on the sealing pin 226 are snapped into position the luer taper nipple 246 (shown in FIG. 8a) on the sealing pin 228 is mated inside a luer taper 252 of the cap 228 to create the air tight seal.

Figure 8C:
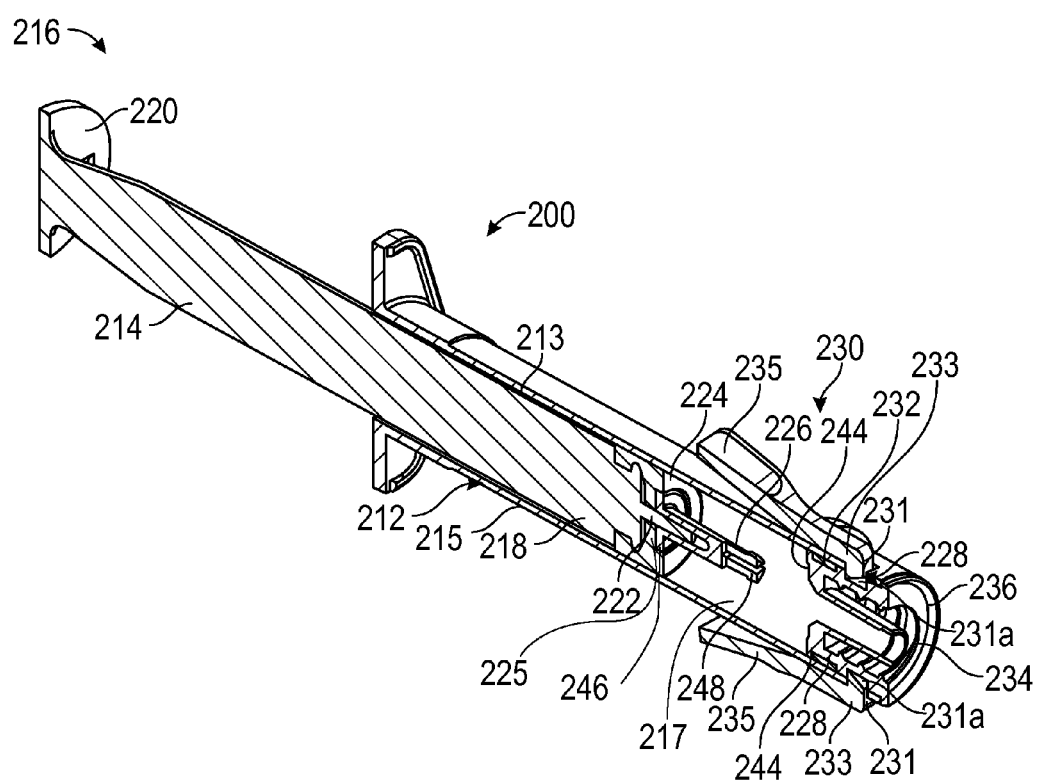

FIG. 8c illustrates a cross sectional view of the embodiment illustrated in FIG. 8a. FIG. 8c shows the plunger shaft 214 disposed within a chamber 213 defined by the outer wall 215 of the syringe body 212. The plunger shaft 212 and the outer wall 215 of the syringe body 212 also define a chamber 217 for holding the lock solution. At the distal end 218 of the plunger 212 is the plunger transfer pin 222 and the plunger seal 224. The plunger seal 224 also includes the sealing pin 226, which is seated within an opening 225 defined by the plunger seal 224. The sealing pin 226 can be transferred to the cap 228 from its opening 225 in the plunger seal 224, when the plunger shaft 214 is pushed through the syringe body 212. The cap 228 can be secured to the syringe body 212 via the pinch release ring 230, and the cap 228 can also be sealed to the syringe body 212 via the cap seal 232. The syringe body 212 includes notches 231, and cap seal 228 has corresponding notches, 231a, both of which can mate with fingers 233 of the pinch ring 230. Flanges 235 can be actuated to engage or disengage the fingers from the notches 231 or 231a. This seal can also be created by molding the cap 228 out of a soft durometer polymer with built in ribs that act as the cap seal.

Figure 8D:
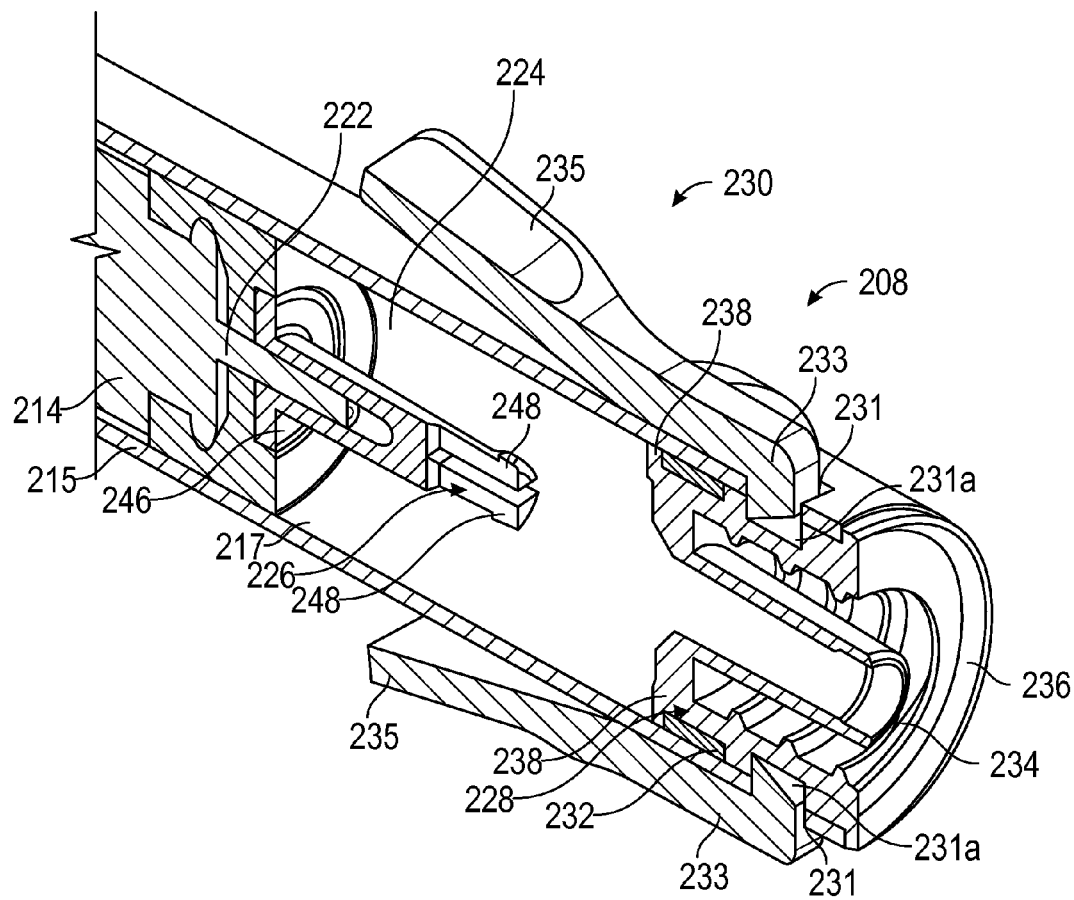

FIG. 8d illustrates a cross sectional view of a distal end 208 of the syringe body 212 in accordance with the embodiment illustrated in FIGS. 8a-8c. FIG. 8d shows the cap 228 disposed at the distal end 208 of the syringe body 212. The cap 228 can be held in place by the pinch release ring 230. The cap 228 can also be sealed to the syringe body 212 via the cap seal 232. The syringe body 212 includes notches 231, and cap 228 has corresponding notches, 231a, both of which can mate with fingers 233 of the pinch ring 230. Flanges 235 can be actuated to engage or disengage the fingers from the notches 231 or 231a. This seal can also be created by molding the cap 228 out of a soft durometer polymer with built in ribs that act as the cap seal.

After all of the lock solution has been transferred from the syringe body 212 through the cap 228 and into the indwelling medical device, the plunger shaft 214, plunger seal 224, syringe body 212 and pinch release ring 230 are then disengaged from the cap 228 by pinching the tabs 235 of the pinch release ring 230 and pulling the assembly from the cap 228 which remains as a seal to the indwelling medical device.

Figure 8E:
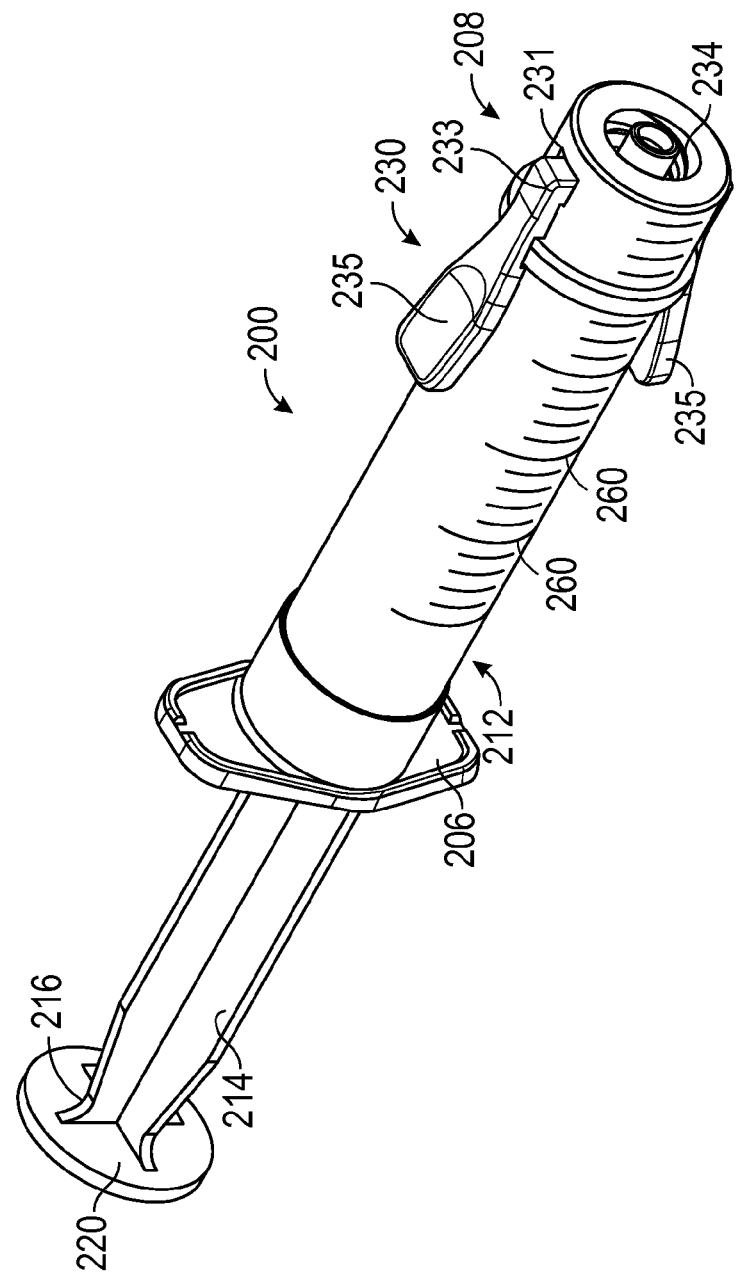

FIG. 8e illustrates the syringe device 200 in accordance with the embodiment of the invention illustrated in FIGS. 8a-8d. FIG. 8e shows the syringe body 212 and the plunger 214 disposed within the syringe body 212. The syringe body 212 includes markings 260 to indicate the amount of lock solution contained within the syringe body 212. The cap 228 (hidden in FIG. 8e) is disposed at the distal end 208 of the syringe body 212 and is held in place by the pinch ring 230. The syringe body 212 includes notches 231, which can mate with fingers 233 of the pinch ring 230. Flanges 235 can be actuated to engage or disengage the fingers from the notches 231 or 231a (hidden in FIG. 8e). Thumb rest 220 is disposed at the proximal end 216 of the plunger shaft 214 and can be used to move the plunger shaft 214 through the syringe body 212 to dispense the lock solution into the indwelling catheter. The syringe body 212 also includes flanges 206 to aid in dispensing the lock solution.

Figure 9A:
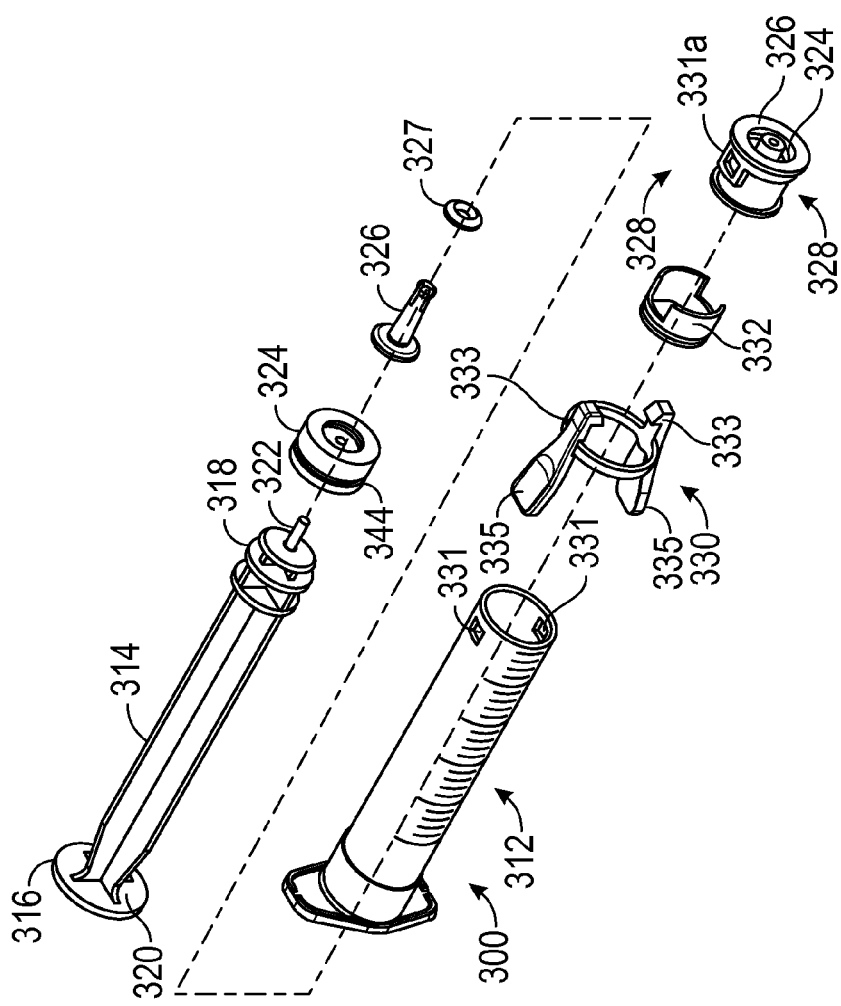
FIGS. 9*a*-9*d* illustrate an integrated syringe device with self-capping connector in accordance with still another embodiment of the invention.

FIG. 9a is another embodiment of the invention and illustrates a pinch clamp 330 to detach a cap 328 from the syringe device 300. FIG. 9a also illustrates a tapered cap-sealing pin 326 and sealing ring 327. The syringe device 300 includes a prefilled syringe body 312 that utilizes a sealing pin 326 for the purpose of infusing a lock solution and sealing the removable catheter cap 328 in one step. The device 300 includes the syringe body 312 and includes a plunger shaft 314 having a proximal end 316 and a distal end 318. The proximal end 316 of the plunger shaft 314 includes a thumb rest 320. The distal end 318 includes or may be connected to a plunger transfer pin 322 and a plunger seal 324. The plunger seal 324 also includes a sealing pin 326 which can be transferred to a cap 328 when the plunger shaft 314 is pushed through the syringe 312. A sealing ring 327 is configured to be disposed around the sealing pin 326 to provide a further seal between the sealing pin 326 and the cap 328. The cap 328 can be secured to the syringe body 312 via the pinch release ring 330, and the cap 328 can also be sealed to the syringe body 312 via the cap seal 332. In order to create the seal, the cap seal 332 can be formed in whole or in part from a soft durometer polymer. Alternatively, this seal can also be created by molding the cap 328 out of a soft durometer polymer with built in ribs that act as the cap seal.

Figure 9B:
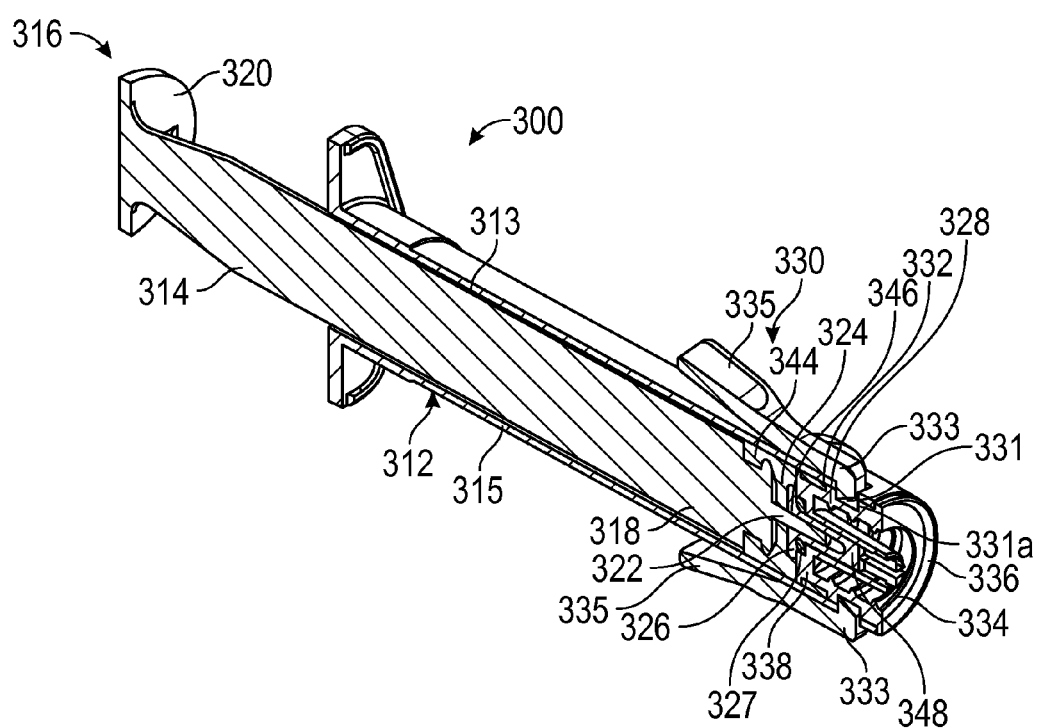
Figure 9C:
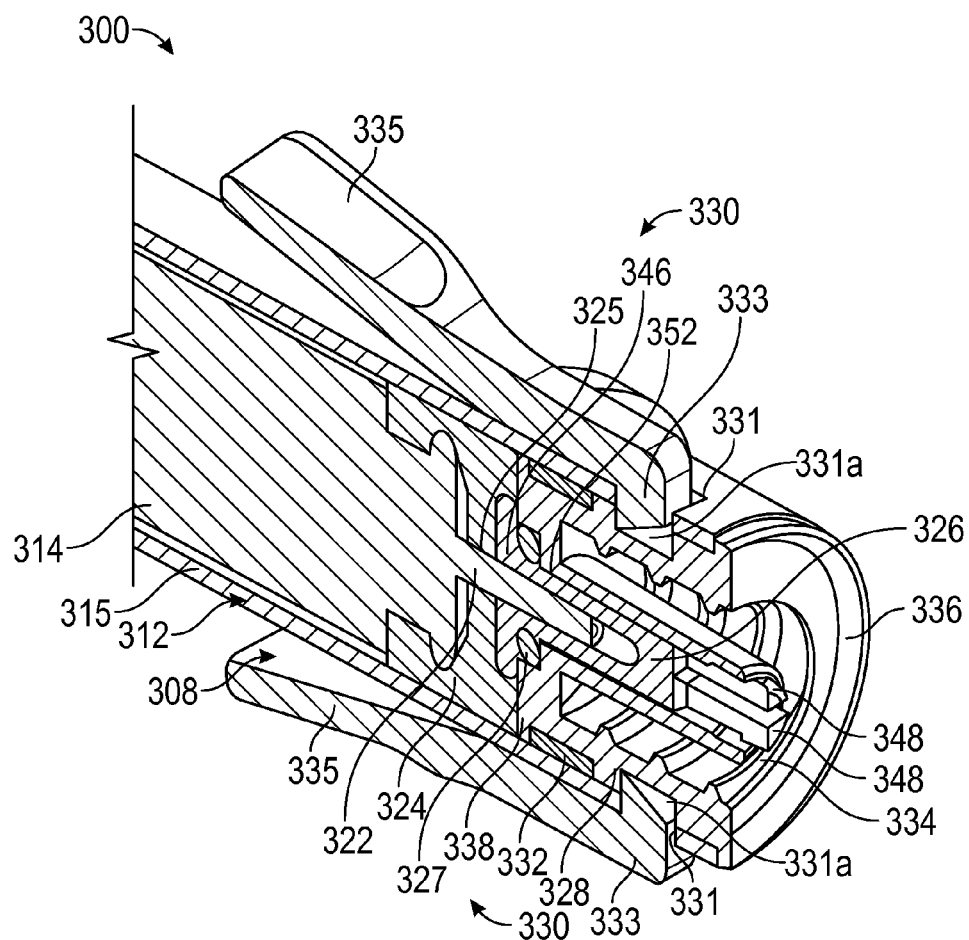

FIG. 9b illustrates a cross sectional view of the embodiment illustrated in FIG. 9a. FIG. 9b shows the plunger shaft 314 disposed within a chamber 313 defined by the outer wall 315 of the syringe body 312. At the distal end 318 of the plunger 312 is the plunger transfer pin 322 and the plunger seal 324. FIGS. 9b and 9c show that the plunger seal 324 also connects to the sealing pin 326, which is seated within an opening 325 defined by the plunger seal 324. The plunger seal pin 326 and seal ring 327 can be transferred to the cap 328 from its opening 325 in the plunger seal 324, when the plunger shaft 314 is pushed through the syringe body 312. The cap 328 can be secured to the syringe body 312 via the pinch release ring 330, and the cap 328 can also be sealed to the syringe body 312 via the cap seal 332. The syringe body 312 includes notches 331, and cap seal 328 has corresponding notches, 331a, both of which can mate with fingers 333 of the pinch ring 330. Flanges 335 can be actuated to engage or disengage the fingers from the notches 331 or 331a. This seal can also be created by molding the cap 328 out of a soft durometer polymer with built in ribs that act as the cap seal.

As further shown in FIG. 9c, the device can be secured to the desired indwelling medical device luer hub via the mating male luer connector 334 on the bottom side 336 of the cap 328. With reference to FIGS. 9b and 9c, the lock solution can be injected into the catheter by depressing the plunger shaft 314 until the sealing pin 326 is driven through the cap 328 and tabs 348 on the bottom side of the sealing pin 326 snap outward upon exiting the bottom side 336 of the cap 328. Once the tabs 348 on the on the sealing pin 326 are snapped into position the luer taper nipple 346 on the sealing pin 328 is mated inside a luer taper 352 of the cap 328 to create the air tight seal.

After all of the lock solution has been transferred from the syringe body 312 through the cap 328 and into the indwelling medical device, the plunger shaft 314, plunger seal 324, syringe body 312 and pinch release ring 330 are then disengaged from the cap 328 by pinching the tabs 335 of the pinch release ring 330 and pulling the assembly from the cap 328 which remains as a seal to the indwelling medical device.

FIG. 9c illustrates a cross sectional view of a distal end 308 of the syringe body 312 in accordance with the embodiment illustrated in FIGS. 9a-9b. FIG. 9c shows the cap 328 disposed at the distal end 308 of the syringe body 312. The cap 328 can be held in place by the pinch release ring 330. The cap 328 can also be sealed to the syringe body 312 via the cap seal 332. The syringe body 312 includes notches 331, and cap seal 328 has corresponding notches, 331a, both of which can mate with fingers 333 of the pinch ring 330. Flanges 335 can be actuated to engage or disengage the fingers from the notches 331 or 331a. This seal can also be created by molding the cap 328 out of a soft durometer polymer with built in ribs that act as the cap seal.

Figure 9D:
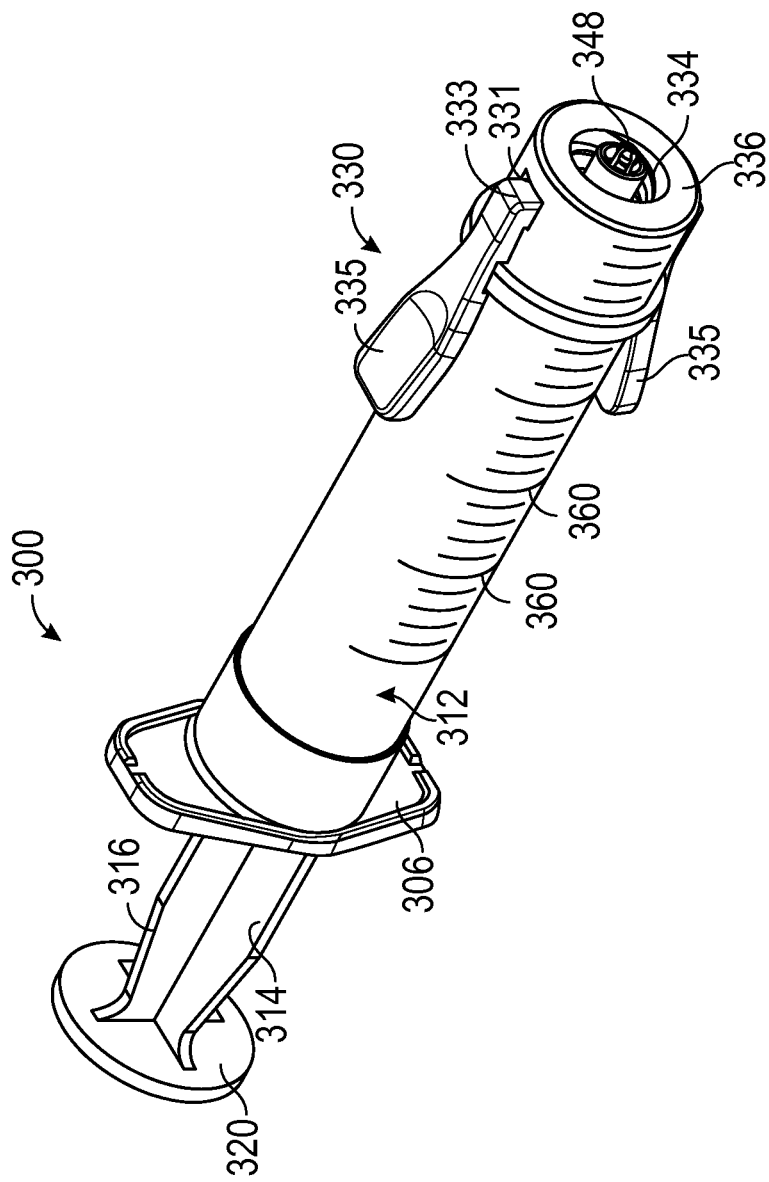

FIG. 9d illustrates the syringe device 300 in accordance with the embodiment of the invention illustrated in FIGS. 9a-9c. FIG. 9d shows the syringe body 312 and the plunger 314 disposed within the syringe body. The syringe body includes markings 360 to indicate the amount of lock solution contained within the syringe body 312. The cap 328 (hidden in FIG. 9a) is disposed at the distal end 308 of the syringe body 312 and is held in place by the pinch ring 330. The syringe body 312 includes notches 331, which can mate with fingers 333 of the pinch ring 330. Flanges 335 can be actuated to engage or disengage the fingers from the notches 331 or 331a (see FIG. 9a). Thumb rest 320 is disposed at the proximal end 316 of the plunger shaft 314 and can be used to move the plunger shaft 314 through the syringe body 312 to dispense the lock solution into the indwelling catheter. The syringe body 312 also includes flanges 306 to aid in dispensing the lock solution.

FIGS. 9b-d illustrate that the cap 328 can be secured to the syringe body 312 via the pinch release ring 330 and the cap 328 is sealed to the syringe body 328 via ribs 344 molded directly on the cap 328. The syringe body 312 includes notches 331 and cap seal 328 has corresponding notches 331a, both of which can mate with fingers 333 of the pinch ring 330. Flanges 335 can be actuated to engage or disengage the fingers from the notches 331 or 331a.

Figure 10A:
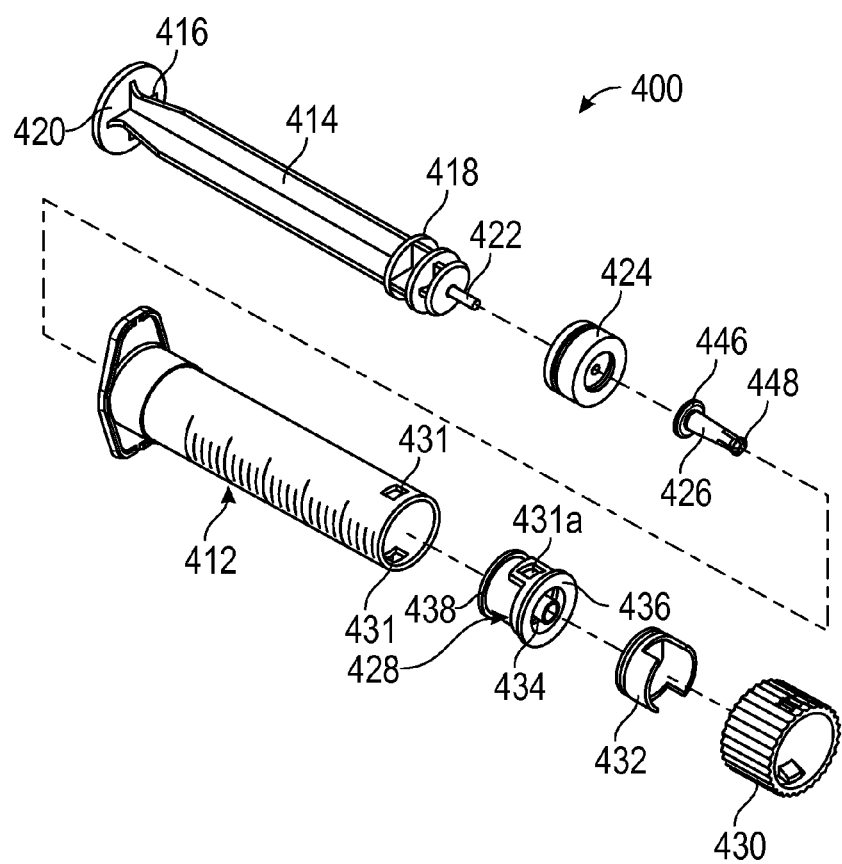
FIGS. 10*a*-10*d* illustrate an integrated syringe device with self-capping connector in accordance with yet another embodiment of the invention.

FIG. 10a is another embodiment of the invention and illustrates a twist clamp 430 to detach a cap 428 from the syringe device 400. FIG. 10a also illustrates a tapered cap-sealing pin 426. The syringe device 400 includes a prefilled syringe body 412 that utilizes a sealing pin 426 for the purpose of infusing a lock solution and sealing the removable catheter cap 428 in one step. The device includes the syringe body 412 includes a plunger shaft 414 having a proximal end 416 and a distal end 418. The proximal end 416 of the plunger shaft 414 includes a thumb rest 420. The distal end 418 includes or may be connected to a plunger transfer pin 422 and a plunger seal 424. The plunger seal 424 also includes a sealing pin 426 which can be transferred to a cap 428 when the plunger shaft 414 is pushed through the syringe 412. The cap 428 can be secured to the syringe body 412 via the pinch release ring 430, and the cap 428 can also be sealed to the syringe body 412 via the cap seal 432. In order to create the seal, the cap seal 432 can be formed in whole or in part from a soft durometer polymer. Alternatively, this seal can also be created by molding the cap 428 out of a soft durometer polymer with built in ribs that act as the cap seal.

The cap 428 can be secured to the syringe body 412 via the twist clamp 430 and the cap 428 is sealed to the syringe body 428 via ribs 444 (shown in FIG. 10b) molded directly on the cap 428. The syringe body 412 includes notches 431 and cap seal 428 has corresponding notches 431a, both of which can mate with fingers 433 of the twist clamp 430.

Figure 10B:
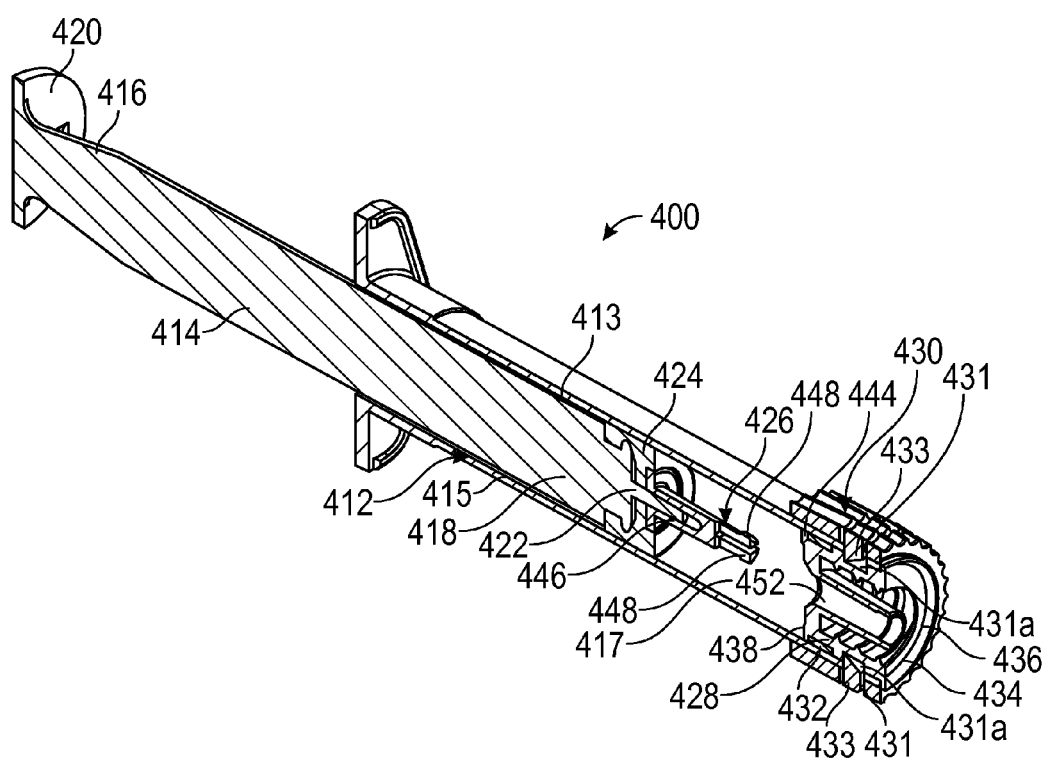

FIG. 10b illustrates a cross sectional view of the embodiment illustrated in FIG. 10a. FIG. 10b shows the plunger shaft 414 disposed within a chamber 413 defined by the outer wall 415 of the syringe body 412. The plunger shaft 412 and the outer wall 415 of the syringe body 412 also define a chamber 417 for holding the lock solution. At the distal end 418 of the plunger 412 is the plunger transfer pin 422 and the plunger seal 424. The plunger seal 424 also includes the sealing pin 426, which is seated within an opening 425 defined by the plunger seal 424. The plunger seal pin 426 can be transferred to the cap 428 from its opening 425 in the plunger seal 424, when the plunger shaft 414 is pushed through the syringe body 412. The cap 428 can be secured to the syringe body 412 via the twist clamp 430, and the cap 428 can also be sealed to the syringe body 412 via the cap seal 432. The syringe body 412 includes notches 431, and cap 428 has corresponding notches, 431a, both of which can mate with fingers 433 of the twist clamp 430. Twisting the clamp 430 compresses the fingers 433 until they mate with the notches 431 and 431a.

This seal can also be created by molding the cap 428 out of a soft durometer polymer with built in ribs that act as the cap seal.

Figure 10C:
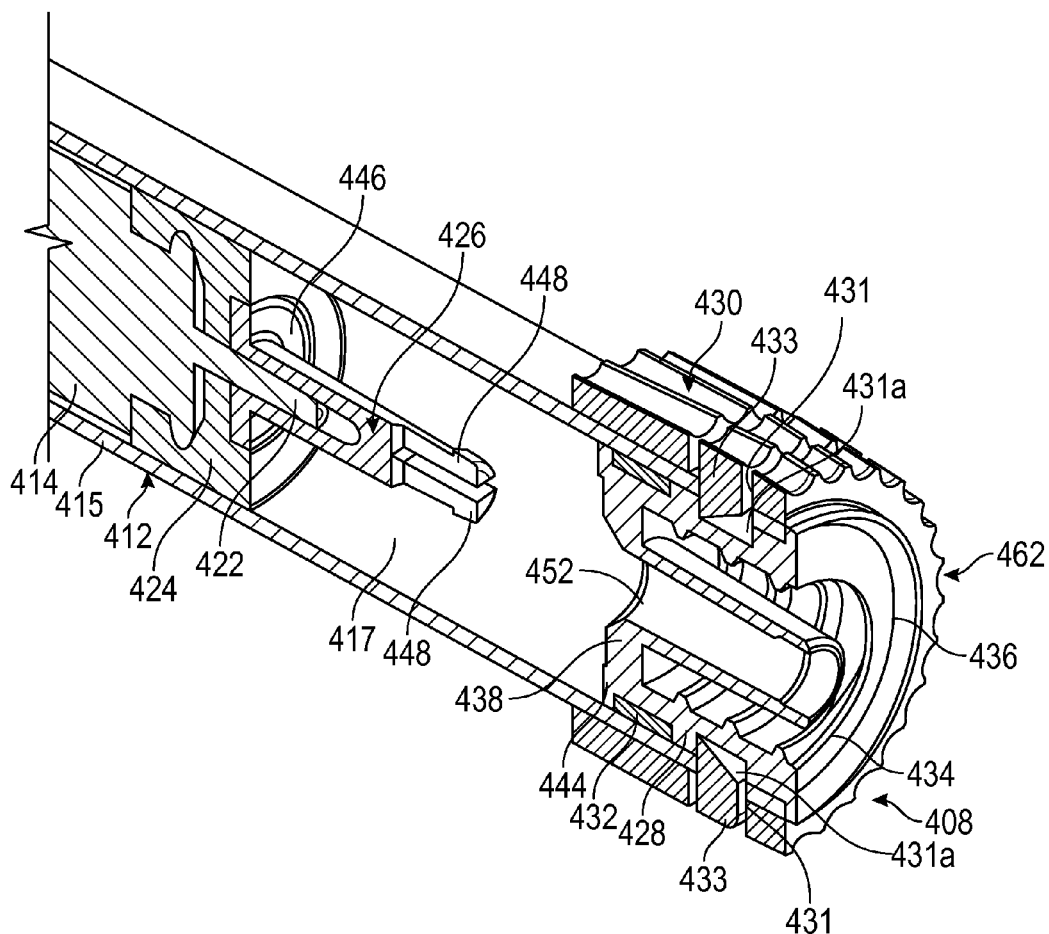
Figure 10D:
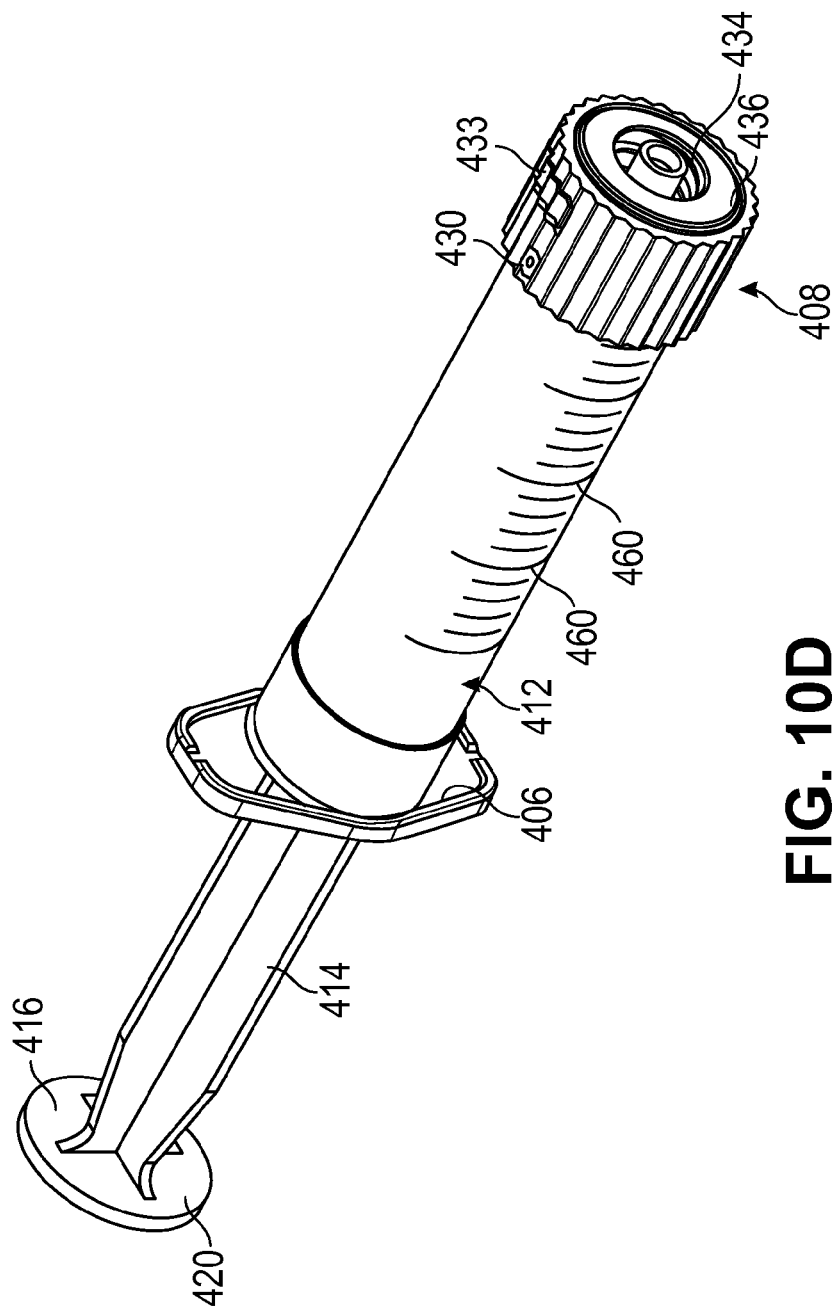

FIGS. 10b-10d illustrate that the device 400 can be secured to the desired indwelling medical device luer hub via the mating male luer connector 434 on the bottom side 436 of the cap 428. As illustrated in FIG. 10b, the lock solution can be injected into the catheter by depressing the plunger shaft 414 until the sealing pin 426 is driven through the cap 428 and tabs 448 on the bottom side of the sealing pin 426 snap outward upon exiting the bottom side 436 of the cap 428. Once the tabs 448 on the on the sealing pin 426 are snapped into position the luer taper nipple 446 on the sealing pin 428 is mated inside a luer taper 452 (best shown in FIG. 10c) of the cap 428 to create the air tight seal.

FIGS. 10b-10d further illustrate that after all of the lock solution has been transferred from the syringe body 412 through the cap 428 and into the indwelling medical device, the plunger shaft 414, plunger seal 424, syringe body 412 and twist clamp 430 are then disengaged from the cap 428 by twisting the twist clamp 430 and pulling the assembly from the cap 428 which remains as a seal to the indwelling medical device.

FIG. 10c illustrates a cross sectional view of a distal end 408 of the syringe body 412 in accordance with the embodiment illustrated in FIGS. 10a-10b. FIG. 10c shows the cap 428 disposed at the distal end 408 of the syringe body 412. The cap 428 can be held in place by the pinch release ring 430. The cap 428 can also be sealed to the syringe body 412 via the cap seal 432. The syringe body 412 includes notches 431, and cap seal 428 has corresponding notches, 431a, both of which can mate with fingers 433 of the twist clamp 430. The twist clamp 430 can include ribs 462 to increase the friction between the clamp 430 and the users fingers to ease removing and applying the twist clamp 430. This seal can also be created by molding the cap 428 out of a soft durometer polymer with built in ribs that act as the cap seal.

FIG. 10d illustrates the syringe device 400 in accordance with the embodiment of the invention illustrated in FIGS. 10a-10c. FIG. 10d shows the syringe body 412 and the plunger 414 disposed within the syringe body 412. The syringe body 412 includes markings 460 to indicate the amount of lock solution contained within the syringe body 412. The cap 428 (hidden in FIG. 10d) is disposed at the distal end 408 of the syringe body 412 and is held in place by the twist clamp 430. Thumb rest 420 is disposed at the proximal end 416 of the plunger shaft 414 and can be used to move the plunger shaft 414 through the syringe body 412 to dispense the lock solution into the indwelling catheter. The syringe body 412 also includes flanges 406 to aid in dispensing the lock solution.

Figure 11:
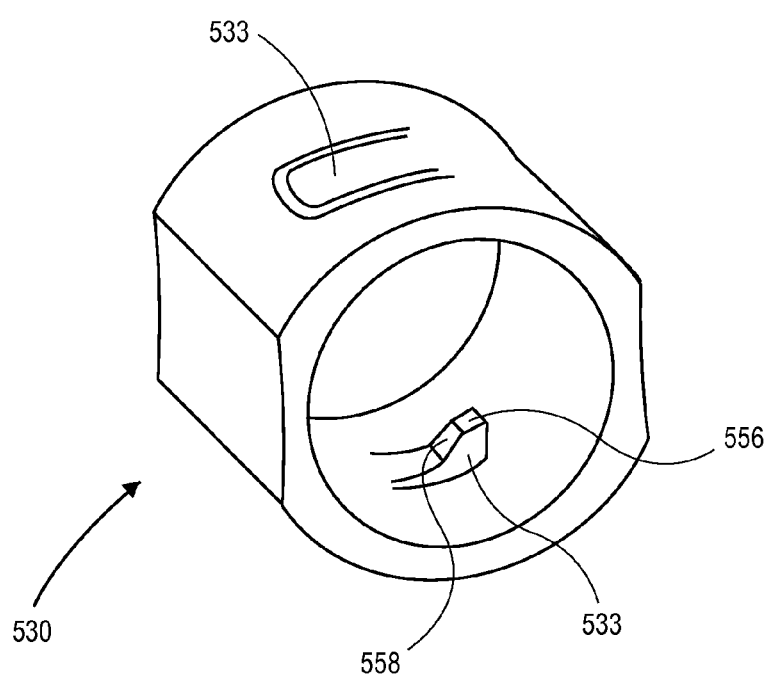
FIG. 11 illustrates an alternate element to the integrated syringe device with self-capping connector in accordance with an embodiment of the invention.

FIG. 11 illustrates an embodiment of the present invention including a twist clamp 530 to detach a sealing cap from a syringe device. A twist clamp 530 secures a cap through pins 533 that extend through the wall of a syringe barrel and engage matching indentations in an external surface of the cap. The flat surfaces 556 of the pins 533 prevent movement of the cap in the axial direction until the clamp 530 is disengaged. Disengagement of the clamp 530 can be accomplished by twisting in a direction such that a bevel 558 in the pin 533 can slide out of windows in the wall of the syringe barrel. Once the pin 530 is slid out of the indentation in the cap and matching window in the syringe barrel, the syringe barrel can be moved axially detaching the cap.

Figure 12A:
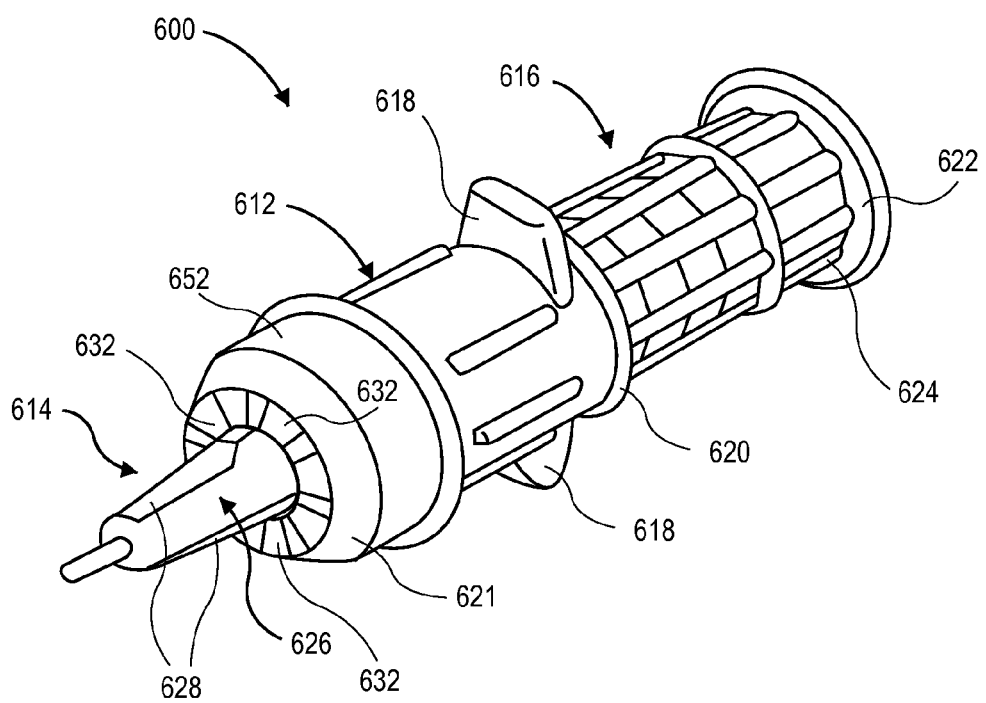
FIGS. 12*a*-12*d* illustrate an integrated syringe device with self-capping connector in accordance with another embodiment of the invention.

FIGS. 12a-12d illustrate another embodiment of the invention. FIG. 12a illustrates a syringe device 600, which includes a prefilled syringe body 612 and an integral end cap 614 which can remain on the catheter after it is locked with the solution. A plunger 616 is disposed within the prefilled syringe body 612 and can be used to dispense the lock solution into the catheter to be locked. The syringe device 600 can also include flanges 618 on the outside surface 620 of the syringe body 612 to aid in dispensing the lock solution. A thumb rest 622 can also be included at a distal end 624 of the plunger 616 to facilitate dispensing the lock solution. The end cap 614 can also include a distal portion 626 which is configured to couple with a luer on the catheter. The distal portion 626 of the end cap 614 includes end cap flanges 628, which further couple with the luer of the catheter. The distal portion 626 of the end cap 614 also can extend past a distal end 621 of the syringe body 612 in order to facilitate injecting the catheter lock solution into the catheter.

Figure 12B:
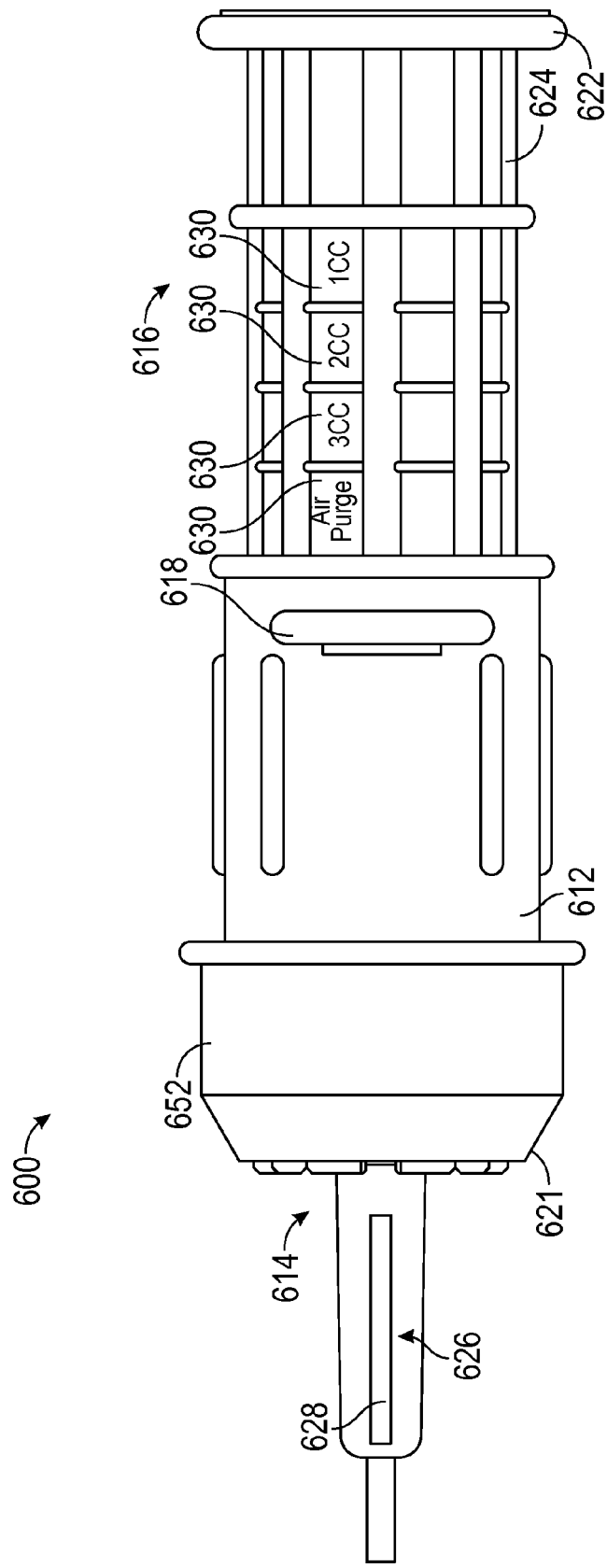

FIG. 12b illustrates the embodiment of the syringe device 600 of FIG. 12a. FIG. 12b shows markings 630 on the plunger 616 which can be used to determine how far to depress the plunger 616 in order to purge air from the syringe device 600. The markings 630 can also indicate the volume of lock solution to be dispensed into the catheter, such 1 cc, 2 cc, 3 cc, or any other applicable measurement of volume. These markings 630 can also indicate other measurements as necessary.

Figure 12C:
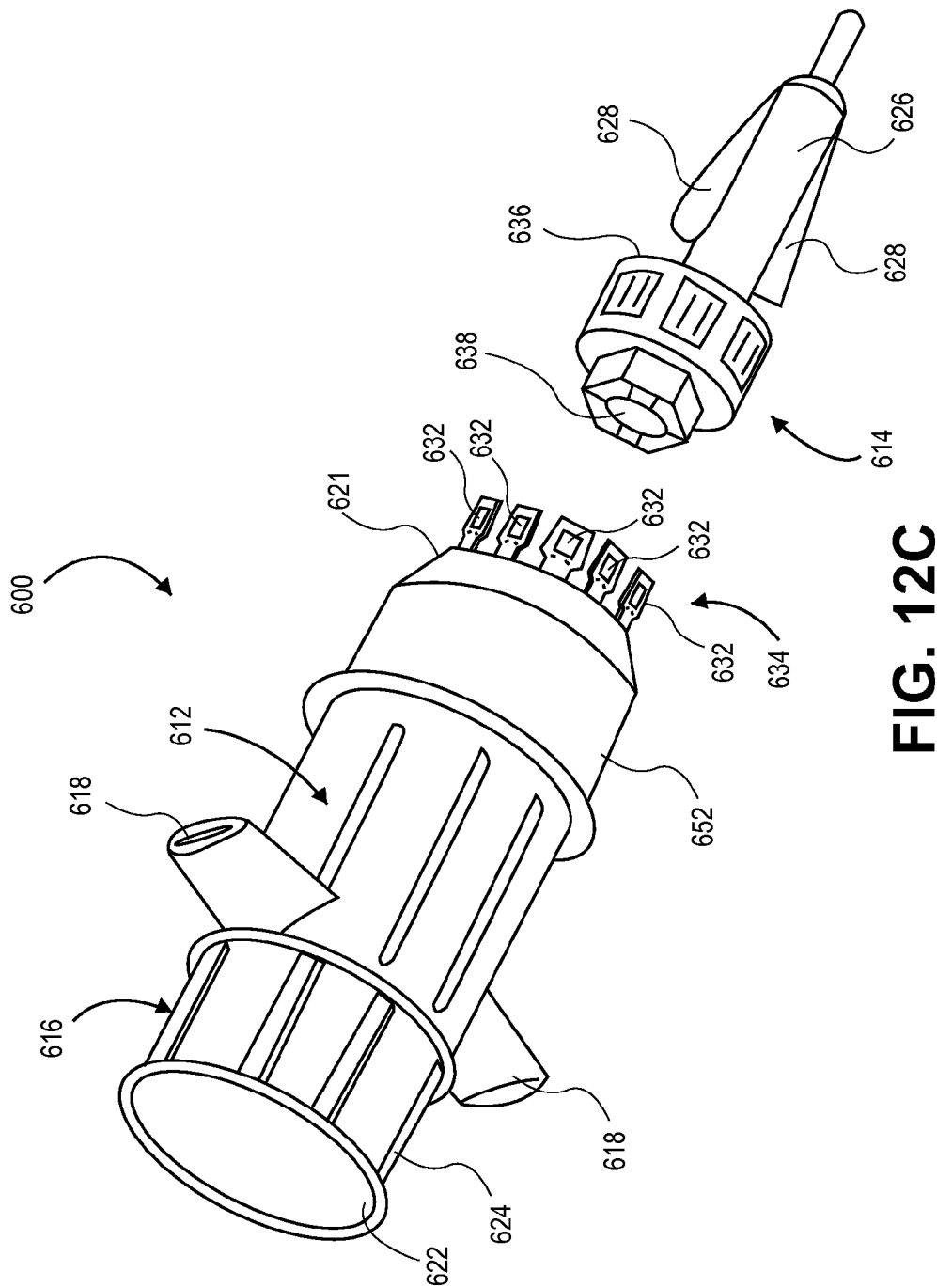

FIG. 12c illustrates an exploded view of the embodiment of the syringe device 600 illustrated in FIGS. 12a and 12b. FIG. 12c illustrates the syringe body 612 having the plunger 616 disposed within an interior of the syringe body 612. The syringe body 612 and plunger 616 portion of the syringe device 600 can be configured to be disposable. Fingers 632 at a distal end 634 of the syringe body 612 can be used to mechanically hold the end cap 614 in place. A slide lock 652 can be used to further hold the fingers 632 against the end cap 614 and can be configured to slideably release the fingers 632, when the user desires to release the end cap 614. As shown in FIG. 12c, the slide lock 652 is in its pulled back position, allowing the fingers 632 to release the end cap 614. The end cap 614 includes a connecting portion 636, a distal portion 626, and an end cap seal portion 638. The distal portion 626 includes end cap flanges 628, which further couple with the luer of the catheter. Also, as noted above, the distal portion 626 of the end cap 614 also can extend past a distal end 621 of the syringe body 612 in order to facilitate injecting the catheter lock solution into the catheter.

Figure 12D:
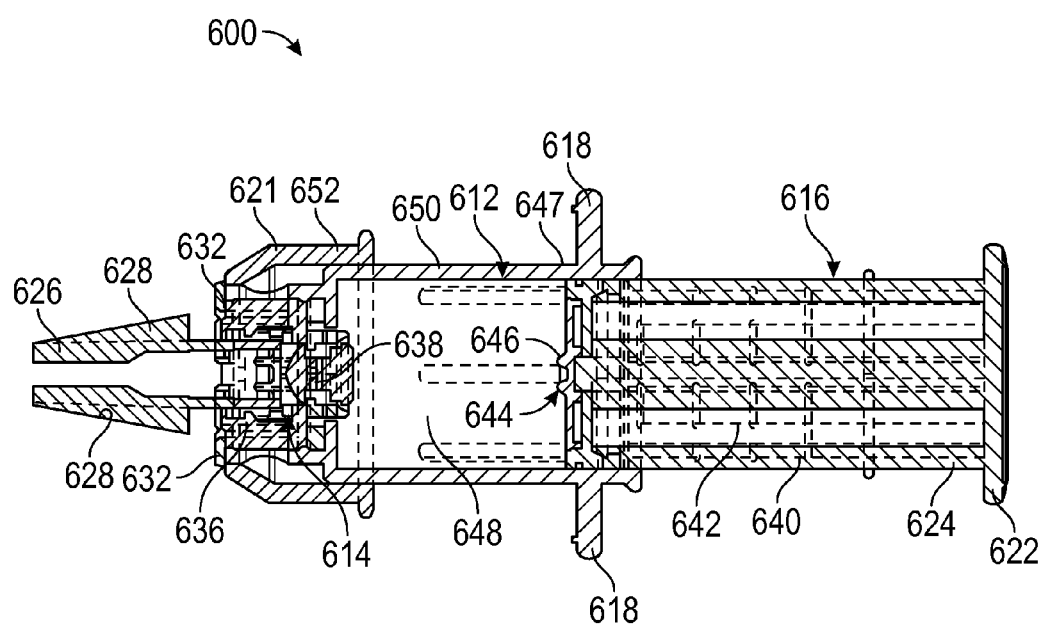

FIG. 12d illustrates a cross-sectional view of the embodiment of the syringe device 600 illustrated in FIGS. 12a-12c. FIG. 12d illustrates the syringe body 612, plunger 616, and end cap 614 of the syringe device 600. An outer wall 640 of the plunger 616 defines a plunger chamber 642, which can hold the lock solution prior to use. The plunger 616 also includes a plunger seal 644 and plunger seal flaps 646. Prior to use, the plunger 616 can be positioned in the syringe body 612. The end-user can pull back the plunger 616 toward a proximal end 647 of the syringe device 600 in order to transfer the catheter lock solution from the plunger chamber 642 to a syringe chamber 648 defined by an outer wall 650 of the syringe body 612. The seal flaps 646 can be configured to open during pull back of the plunger 616 allowing the catheter lock solution to flow into the syringe chamber 648. The end-user can then advance the plunger 616 to a first predetermined distance to remove all of the air in the syringe chamber 648, which is referred to as "air purge."

Further, as illustrated in FIG. 12d, the end cap 614 is frictionally held in place by fingers 632. The end cap 614 can include a connecting portion 636 configured to couple to the catheter. For instance if the catheter includes a luer on its end the end cap 614 can be threaded to allow for it to be tightened onto the luer of the catheter. Any other suitable configuration for coupling the end cap 614 to the catheter can also be used, such as snapping onto the catheter or being frictionally held on the catheter. The end cap 614 can further include an end cap seal portion 638. Advancing the plunger 616 further past the first predetermined distance creates positive pressure within the syringe device and can therefore open the end cap seal portion 638, in order to transfer the catheter lock solution into the catheter. Conversely, negative pressure, in the form of aspiration would prevent passage of solution through the end cap seal portion 638. Once the syringe device 600 has been purged of air, by advancing the plunger to the first predetermined distance, the syringe device can be coupled to the catheter via the connecting portion 636. The end-user can then advance the plunger 616 to a second predetermined distance in order to infuse a predetermined amount of catheter lock solution past the end cap seal into the catheter. Once the catheter is filled with solution, the end-user can deploy the end cap 614 from the syringe device 600 by pulling back on the slide lock 652. Once fully deployed, the end cap 614 can reside on the catheter, and the catheter would be fully flushed and sealed with the catheter lock solution.

Other embodiments could include, a needless connector housed within the delivery system deemed compatible with the lock solution contained in the syringe, color coding on catheter and needless connector, labeled catheter, end-cap and delivery system, or a lock solution filled glass container contained within the plunger reservoir whereby one the plunger is pulled back the container would be cracked to release the lock solution and subsequently fill the barrel reservoir.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for infusing liquid and sealing an indwelling medical device comprising:
    a syringe body having an outer wall defining a lumen extending therethrough for holding an infusing liquid and further including a proximal end and a distal end and wherein the outer wall defines an opening at the distal end of the syringe body;
    a plunger slidably disposed within the lumen of the syringe, such that the plunger slides from the proximal end of the syringe body to the distal end of the syringe body;
    a first notch defined by the outer wall of the syringe body and positioned proximate of the opening at the distal end of the syringe body;
    a pinch release ring having a finger which couples with the first notch and a wing to provide leverage to remove the finger from the first notch;
    a cap defining an opening through which the infusing liquid can travel, disposed within the opening at the distal end of the syringe body configured to couple to an end of the indwelling medical device and wherein the cap defines a second notch with which the finger of the pinch release ring can couple; and
    a plunger seal disposed at a proximal end of the plunger, and configured to be separable from the proximal end of the plunger and coupleable to the cap, such that the cap is sealed when coupled to the plunger seal.

2. An apparatus for infusing liquid and sealing an indwelling medical device comprising:
    a syringe body having an outer wall defining a lumen extending therethrough and further including a proximal end and a distal end and wherein the outer wall defines an opening at the distal end of the syringe body;
    a plunger having a proximal end and a distal end slidably disposed within the lumen of the syringe body, such that the plunger slides from the proximal end of the syringe to the distal end of the syringe body;
    a cap disposed at the distal end of the syringe body within the opening of the lumen defined by the outer wall of the syringe body configured to couple to an end of the indwelling medical device and wherein the cap is configured to be separated from the syringe body; and
    a plunger seal disposed at a proximal end of the plunger, and configured to be separable from the proximal end of the plunger and coupleable to the cap, such that the cap is sealed.

3. The apparatus of claim 2, further comprising a sealing pin disposed at the proximal end of the plunger configured to be coupled to the cap to form a seal, wherein the sealing pin is removable from the proximal end of the plunger.

4. The apparatus of claim 3, further comprising slits in the sealing pin to allow the sealing pin to deform while sliding into place and then spring back to a non-deformed position when the sealing pin in located in the cap.

5. The apparatus of claim 2, further comprising a sealing ball disposed at the proximal end of the plunger configured to be coupled to the cap to form a seal, wherein the sealing ball is removable from the proximal end of the plunger.

6. The apparatus of claim 2, further comprising a sliding lock disposed at the distal end of the syringe body, slidably disposed to frictionally hold the fingers around the cap in a first position and to release the fingers from around the cap in a second position.

7. The apparatus of claim 6, wherein the plunger has an outer wall defining a hollow elongate shaft and the cap includes a cap seal.

8. The apparatus of claim 2, wherein the plunger further includes a projection configured to contact a sealing member when the plunger moves toward the distal end of the syringe body.

9. The apparatus of claim 8, wherein the sealing member pushed by the plunger projection into the cap to seal the cap.

10. The apparatus of claim 2, wherein the plunger seal is annular.

11. The apparatus of claim 2, further comprising:
    a first notch defined by the outer wall of the syringe body and positioned proximate of the opening at the distal end of the syringe body;
    a pinch release ring having a finger which couples with the first notch and a threads for attaching the pinch release ring to the syringe body; and
    a cap defining an opening through which the infusing liquid can travel, disposed within the opening at the distal end of the syringe body configured to couple to an end of the indwelling medical device and wherein the cap defines a second notch with which the finger of the pinch release ring can couple.

12. The apparatus of claim 2, wherein the cap is separated from the syringe body by one of unscrewing, sliding, and breaking.

13. The apparatus of claim 2, wherein the plunger includes latch elements configured to enter into the sealing element.

* * * * *